United States Patent
Ohnishi

(10) Patent No.: US 8,649,850 B2
(45) Date of Patent: Feb. 11, 2014

(54) PROBE FOR DETECTING SUBSTANCE IN BODY AND SYSTEM FOR DETECTING SUBSTANCE IN BODY MAKING USE OF THE PROBE

(75) Inventor: Michihiro Ohnishi, Kanagawa (JP)

(73) Assignee: Sony Corporation, Tokyo (JP)

( * ) Notice: Subject to any disclaimer, the term of this patent is extended or adjusted under 35 U.S.C. 154(b) by 602 days.

(21) Appl. No.: 12/886,955

(22) Filed: Sep. 21, 2010

(65) Prior Publication Data

US 2011/0082354 A1 Apr. 7, 2011

(30) Foreign Application Priority Data

Oct. 1, 2009 (JP) .............................. P2009-229567
Dec. 9, 2009 (JP) .............................. P2009-279758
Apr. 5, 2010 (JP) .............................. P2010-087060
Jul. 5, 2010 (JP) .............................. P2010-153058

(51) Int. Cl.
*A61B 6/00* (2006.01)

(52) U.S. Cl.
USPC ............................. 600/476; 600/407; 600/473

(58) Field of Classification Search
USPC ......................................... 600/407, 473, 476
See application file for complete search history.

(56) References Cited

U.S. PATENT DOCUMENTS

| | | | |
|---|---|---|---|
| 4,452,901 A * | 6/1984 | Gordon et al. ................ | 435/7.92 |
| 5,334,503 A * | 8/1994 | Snyder et al. ................ | 435/7.32 |
| 5,582,705 A * | 12/1996 | Yeung et al. ................ | 204/603 |
| 5,736,341 A * | 4/1998 | Sorsa et al. ................ | 435/7.1 |
| 6,103,199 A * | 8/2000 | Bjornson et al. ............... | 422/503 |
| 2005/0221279 A1* | 10/2005 | Carter et al. ....................... | 435/4 |
| 2007/0042315 A1* | 2/2007 | Boutoussov et al. ........... | 433/29 |
| 2009/0312319 A1* | 12/2009 | Ren et al. ................... | 514/234.2 |

FOREIGN PATENT DOCUMENTS

| | | |
|---|---|---|
| JP | 2001-201437 | 7/2001 |
| JP | 2005-283366 | 10/2005 |

OTHER PUBLICATIONS

Colston et al.—Intraoral Fiber-Optic-Based Diagnostic for Periodontal Disease—Jan. 21, 2000—International Symposium on Biomedical Optics—pp. 1-10.*

* cited by examiner

*Primary Examiner* — James Kish
(74) *Attorney, Agent, or Firm* — K&L Gates LLP

(57) ABSTRACT

Disclosed is a probe for detecting a substance in the body in gingival crevicular fluid. The probe includes a gingival sulcus insert section and a sensitive part. The gingival sulcus insert section can be inserted into a gingival sulcus. The sensitive part is arranged on the gingival sulcus insert section and contains a detection substance for permitting optical detection of the substance in the body. A system for detecting a substance in the body is also disclosed. The system for detecting a substance in the body includes the probe for detecting a substance in the body, a light irradiator for irradiating light onto the sensitive part in the probe, and a photodetector for detecting optical information from an inside of the sensitive part upon irradiation of light by the light irradiator.

18 Claims, 20 Drawing Sheets

100 mg/dL D-GLUCOSE/PBS

BRIGHT-FIELD IMAGE

FLUORESCENT IMAGE

VENT (0.05mm diameter)

BRIGHT-FIELD IMAGE

FLUORESCENT IMAGE

PROBE FOR DETECTING SUBSTANCE IN BODY AND SYSTEM FOR DETECTING SUBSTANCE IN BODY MAKING USE OF THE PROBE

CROSS REFERENCES TO RELATED APPLICATIONS

The present application claims priority to Japanese Priority Patent Applications JP 2009-229567 filed in the Japan Patent Office on Oct. 1, 2009; JP 2009-279758 filed in the Japan Patent Office on Dec. 9, 2009; JP 2010-087060 filed in the Japan Patent Office on Apr. 5, 2010 and JP 2010-153058 filed Japan Patent Office on Jul. 5, 2010, the entire contents of which is hereby incorporated by reference.

BACKGROUND

This application relates to a probe for detecting a substance in the body useful as an instrument for detecting a substance in the body in gingival crevicular fluid. More specifically, the present application is concerned with a probe for detecting a substance in the body for permitting optical detection of a substance in the body in gingival crevicular fluid and also with a system for detecting a substance in the body making use of the probe for detecting a substance in the body.

For the detection of a substance in the body, it is generally a common practice to collect blood and then to optically or electrically analyze the substance in the body in the blood. However, the collection of blood is an invasive method, needs medical qualifications or the like for a phlebotomist, and moreover, is costly. Further, purification of blood is needed in actual detection or measurement, thereby involving a problem in that labor and time are needed to obtain the detection or measurement results. In addition, continuous measurement requires an increased number of sampling, so that a substantial burden is imposed on a subject under test. There is, accordingly, another problem in that no real-time measurement is feasible.

Therefore, a variety of methods have been being developed in recent years to reduce the invasiveness to the body. Taking as an example the measurement of blood sugar level, noninvasive and low-invasive measuring methods will be described hereinafter.

The noninvasive measuring methods include a method that is applied to the dermis, arm, finger tip or the like and determines the glucose level in blood by measuring a scattering transmission spectrum with infrared light, a method that is applied to the labial mucosa and determines the glucose level in blood by measuring a scattering spectrum with infrared light, a method that is applied to the finger tip and determines the glucose level in blood by measuring a Raman scattering spectrum, and a method that is applied to the skin and determines the glucose level in blood by performing photoacoustic measurement.

These noninvasive measuring methods are, however, accompanied by a problem in that they are inferior in accuracy to the measuring method that relies upon the collection of blood although they can measure the blood glucose level in real time.

On the other hand, the low-invasive measuring methods include a method that measures the glucose level in body fluid (intercellular fluid) by collecting the body fluid from the arm on the same principle of iontophoresis, a method that measures the glucose level in body fluid by collecting the body fluid from the skin under ultrasonic waves, a method that measures the glucose level in body fluid by collecting the body fluid from the arm with a patch or cannula, a method that measures the glucose level in lacrimal fluid by collecting the lacrimal fluid from the eye and conducting fluorescent measurement, a method that measures the glucose level in lacrimal fluid by collecting the lacrimal fluid from the eye and conducting holographic diffraction, a method that measures the glucose level in saliva by collecting the saliva from the mouth, and a method that measures the glucose level in urine by collecting the urine.

These low-invasive measuring methods are, however, accompanied by problems such that they cannot perform real-time measurement because the glucose level in body fluid is delayed by 30 minutes or so compared with the corresponding glucose level in blood, that they are difficult to perform accurate measurement of the concentration of glucose because the concentration of glucose in body fluid, lacrimal fluid, saliva or urine is as low as $1/10$ or less of the concentration of glucose in blood, and that they can hardly perform accurate measurement of a glucose level because stable sampling is difficult for the collection of saliva from the mouth.

In the meantime, a method has been under development as a noninvasive measuring method to detect a substance in the body in gingival crevicular fluid. It is known that the glucose level, for example, in gingival crevicular fluid changes with time in substantial conformity with the glucose level in blood. It is, therefore, possible to perform the diagnosis, treatment and control of diabetes by measuring the glucose level in gingival crevicular fluid.

Concerning the activity of aspartic acid aminotransferase (AST) and that of alanine aminotransferase (ALT) as parameters of liver function, on the other hand, their values in gingival crevicular fluid are known to correlate to the corresponding values in blood. It is, therefore, possible to determine the degree of a loss of liver function by measuring the AST activity and ALT activity in gingival crevicular fluid.

As a technology for measuring a substance in the body in gingival crevicular fluid as described above, Japanese Patent Laid-open No. 2001-201437 discloses a technology relating to a capillary device that can draw up gingival crevicular fluid under capillary action based on a concept to noninvasively estimate biological information such as a glucose level from the concentration of a chemical substance contained in gingival crevicular fluid.

Further, Japanese Patent Laid-open No. 2005-283366 discloses a collection instrument which as viewed in transverse section, is formed of a shell portion and plural rib portions extending in centripetal directions from the shell portion. Between these rib portions, a plurality of capillary passages are formed through the collection instrument from its one end to its opposite end to draw up fluid. The collection instrument can, therefore, collect body fluid in a predetermined constant microamount as small as several microliters or less from a site of collection in a pinpoint manner.

These technologies, however, need cumbersome handling of a sample, are time-consuming and laborious and require skill, because they rely upon a method that collects body fluid such as gingival crevicular fluid with the above-described capillary device or collection instrument and then measures the level of a substance in the body in the collected body fluid. In addition, it is necessary for continuous measurement to frequently perform sampling. As a matter of fact, the above-described technologies cannot measure the level of a substance in the body in real time.

SUMMARY

As mentioned above, technologies have been developed in recent years to perform the diagnosis, treatment and control of various diseases by measuring substances in the body in gingival crevicular fluid. It is, however, the current situation that like the technology disclosed in Japanese Patent Laid-open No. 2001-201437, none of such technologies have reached yet to such a technology as permitting real-time measurement of a substance in the body in gingival crevicular fluid. There is another problem in that, because a sample is collected from the gingival sulcus, that is, a very narrow site, gingival crevicular fluid can be collected only in a small amount and the stability of measurement accuracy cannot be maintained.

The present application, therefore, desirably provides a technology that can noninvasively measure a substance in the body in gingival crevicular fluid in real time and with high accuracy.

To achieve the above-descried desire, the present inventors have enthusiastically carried out research. As a result, the present inventors fundamentally changed the idea of collecting gingival crevicular fluid, and came up with an idea of measuring a substance in the body in gingival crevicular fluid, leading to the completion of the application.

In one mode of the application, there is thus provided a probe for detecting a substance in the body for detecting a substance in the body in gingival crevicular fluid, including a gingival sulcus insert section that can be inserted into a gingival sulcus, and a sensitive part arranged on the gingival sulcus insert section and containing a detection substance for permitting optical detection of the substance in the body. Preferably, the probe may further include an optical waveguide for performing at least one of irradiation of light onto the sensitive part and detection of light from the sensitive part. The optical waveguide may be formed, for example, from an optical fiber.

The gingival sulcus insert section may preferably have a short side or short axis of not greater than 0.2 mm.

Preferably, the gingival sulcus insert section may be provided with a capillary portion through which the gingival crevicular fluid can be collected under capillary action, and the gingival crevicular fluid may be introduced to the sensitive part via the capillary portion. The sensitive part may preferably be arranged on an inner wall of the capillary portion, and the detection substance is immobilized in the sensitive part. The optical waveguide may preferably be connected to a cylindrical side wall of the capillary portion. The immobilization may have been achieved, for example, through a photoreaction.

Preferably, the detection substance may cause a change in fluorescence intensity when the detection substance specifically binds to the substance in the body. The detection substance may be, for example, a boronic acid compound. As a preferred alternative, the detection substance may include (1) at least one enzyme and (2) a substance that can become a target of optical measurement.

Preferably, the substance that can become the target of the optical measurement may be a substance that is converted to a fluorescence source through a reaction with hydrogen peroxide as a product of an enzyme reaction. The fluorescence source may be, for example, resorufin. As a preferred alternative, the substance that is capable of becoming the subject of the target of the optical measurement may be a substance whose absorbance changes through a reaction with hydrogen peroxide as a product of an enzyme reaction. The substance the absorbance of which changes may be, for example, o-dianisidine.

The detection substance may include (1) a first enzyme for catalyzing a first reaction in which the substance in the body in the gingival crevicular fluid takes part and a second enzyme for catalyzing a second reaction in which a product formed by the first reaction takes part, and (2) a substance that can become a target of optical measurement. The first enzyme may be selected, for example, from the group including glucose oxidase, alcohol oxidase, uricase (urate oxidase), lactate oxidase, fructosyl-amino acid oxidase, sarcosine oxidase, and cholesterol oxidase. The second enzyme may be, for example, peroxidase.

In another mode of the application, there is also provided a system for detecting a substance in the body for detecting a substance in the body in gingival crevicular fluid, including a probe for detecting a substance in the body provided with a gingival sulcus insert section that can be inserted into a gingival sulcus, and a sensitive part arranged on the gingival sulcus insert section and containing a detection substance for permitting optical detection of the substance in the body; a light irradiator for irradiating light onto the sensitive part in the probe for detecting a substance in the body; and a photodetector for detecting optical information from an inside of the sensitive part upon irradiation of light by the light irradiator. Preferably, the system may further include a dichroic element for extracting optical information from the inside of the sensitive part upon irradiation of light by the light irradiator.

According to the present application, a substance in the body in gingival crevicular fluid can be measured in the gingival sulcus, so that the substance in the body in the gingival crevicular fluid can be noninvasively measured in real time and with high accuracy.

Additional features and advantages are described herein, and will be apparent from the following Detailed Description and the figures.

BRIEF DESCRIPTION OF THE FIGURES

FIGS. 25A and 25B are fluorescent observation images of a sensitive part, which was formed on an inner wall of a capillary by using a similar aqueous photoimmobilizing solution as that in Example 10, as observed from the side and at a cross-section, respectively;

FIG. 26 is a graph showing the results of fluorescence measurement at different D-glucose concentrations by a probe with a sensitive part formed on an inner wall of a capillary and a fluorophotometer connected to the probe;

FIG. 27 is a graph showing the results of fluorescence detection and measurement of ethanol by a probe with a sensitive part formed on an inner wall of a capillary and a fluorophotometer connected to the probe;

FIG. 28 is a graph showing the results of fluorescence measurement for the detection of D-glucose as conducted by using a similar probe as the detection probe adopted in Example 13;

FIG. 29 is a graph showing the results of fluorescence detection and measurement of uric acid by a probe with a sensitive part formed on an inner wall of a capillary and a fluorophotometer connected to the probe;

FIG. 30 is a graph showing the results of fluorescence detection and measurement of lactic acid by a probe with a sensitive part formed on an inner wall of a capillary and a fluorophotometer connected to the probe;

FIG. 31 is a graph showing the results of fluorescence detection and measurement of glycated albumin and albumin by a probe with a sensitive part formed on an inner wall of a capillary and a fluorophotometer connected to the probe;

FIGS. 32A and 32B are graphs showing the results of fluorescence detection and measurement of creatinine and creatine by a probe with a sensitive part formed on an inner wall of a capillary and a fluorophotometer connected to the probe. It is to be noted that creatininase was contained in the fluorescence detection and measurement the results of which are shown in FIG. 32A but was not contained in the fluorescence detection and measurement the results of which are shown in FIG. 32B;

FIGS. 33A and 33B are graphs showing the results of fluorescence detection and measurement of cholesterol and a mixed sample solution by a probe with a sensitive part formed on an inner wall of a capillary and a fluorophotometer connected to the probe. It is to be noted that cholesterol esterase was contained in the fluorescence detection and measurement the results of which are shown in FIG. 33A but was not contained in the fluorescence detection and measurement the results of which are shown in FIG. 33B.

DETAILED DESCRIPTION

Figure 1:
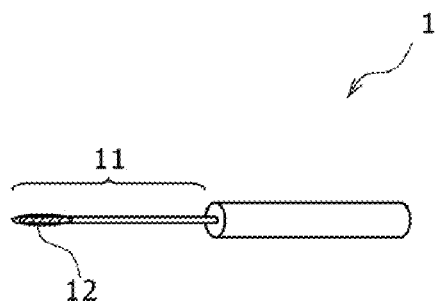
FIG. 1 is a schematic conceptual diagram of a first embodiment of the probe for detecting a substance in the body according to the present application.
Figures 2A, 2B, 2C, 2D, 2E, 2F:
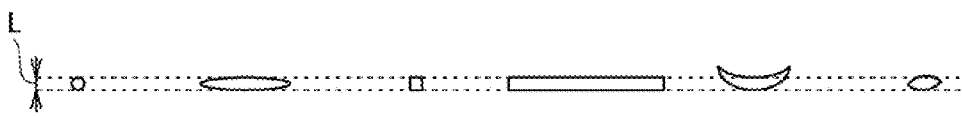
FIGS. 2A through 2F are schematic cross-sectional diagrams illustrating, by way of example, cross-sectional shapes of the gingival sulcus insert section of the probe for detecting a substance in the body according to the present application.

With reference to the accompanying drawings, a description will hereinafter be made about certain preferred embodiments for carrying out the present application. It is to be noted that the embodiments to be described hereinafter merely indicate some examples of representative embodiments of the application and that the scope of the application shall no be narrowly interpreted by the following embodiments. The description will be made in the following order.

1. Probe 1 for Detecting a Substance in the Body (1) Gingival sulcus insert section 11

(2) Sensitive part 12

(2-1) Where the substance in the body is a saccharide (2-1-1) Substance in the body: saccharide/detection substance: boronic acid compound (2-1-2) Substance in the body: glucose/detection substances: glucose oxidase, peroxidase, and 10-acetyl-3,7-dihydroxyphenoxazine (ADHP)

(2-2) Where the substance in the body is an alcohol (2-2-1) Substance in the body: alcohol/detection substances: alcohol oxidase, peroxidase, and 10-acetyl-3,7-dihydroxyphenoxazine (ADHP)

(2-3) Where the substance in the body is a purine derivative (2-3-1) Substance in the body: uric acid/detection substances: uricase, peroxidase, and 10-acetyl-3,7-dihydroxyphenoxazine (ADHP)

(2-4) Where the substance in the body is a glycolytic product (2-4-1) Substance in the body: lactic acid/detection substances: lactate oxidase, peroxidase, and 10-acetyl-3,7-dihydroxyphenoxazine (ADHP)

(2-5) Where the substance in the body is a glycated protein (2-5-1) Substance in the body: glycated albumin or albumin/detection substances: protease, fructosyl-amino acid oxidase, peroxidase, and 10-acetyl-3,7-dihydroxyphenoxazine (ADHP)

(2-5-2) Substance in the body: glycated albumin or albumin/detection substances: component (a): protease, and components (b): fructosyl-amino acid oxidase, peroxidase, and 10-acetyl-3,7-dihydroxyphenoxazine (ADHP)

(2-6) Where the substance in the body is an amino acid (2-6-1) Substance in the body: creatinine or creatine/detection substances: creatininase, creatinase, sarcosine oxidase, peroxidase, and 10-acetyl-3,7-dihydroxyphenoxazine (ADHP)

(2-6-2) Substance in the body: creatinine or creatine/detection substances: creatinase, sarcosine oxidase, peroxidase, and 10-acetyl-3,7-dihydroxyphenoxazine (ADHP)

(2-7) Where the substance in the body is a lipid (2-7-1) Substance in the body: cholesterol or cholesteryl ester/detection substances: cholesterol esterase, cholesterol oxidase, peroxidase, and 10-acetyl-3,7-dihydroxyphenoxazine (ADHP)

(2-7-2) Substance in the body: cholesterol or cholesteryl ester/detection substances: cholesterol oxidase, peroxidase, and 10-acetyl-3,7-dihydroxyphenoxazine (ADHP)

(2-8) Other candidate examples of the substance in the body (3) Optical waveguide 13

(4) Capillary portion 14

2. System 10 for Detecting a Substance in the Body (1) Light irradiator 15

(2) Photodetector 16

(3) Dichroic element 17

(4) Collective lens 18

(5) Optical filter 19

1. Probe for detecting a substance in the body

Referring to FIG. 1, the first embodiment of the probe 1 for detecting a substance in the body according to the present application will be descried. The probe 1 for detecting a substance in the body according to the present application is an instrument for detecting a substance in the body in gingival crevicular fluid, and roughly dividing, is provided with at least a gingival sulcus insert section 11 and a sensitive part 12. In addition, it may also be provided with an optical waveguide 13 and a capillary portion 14 as needed. These elements will each be described in detail hereinafter.

The term "gingival crevicular fluid" as used herein means a fluid existing in a gingival sulcus and containing substances in the body from the dental tissue. Specifically, gingival sulcus exudate (GCF: fluid containing plasma components and tissue fluid components exuded from the gingiva), blood emitted from the gingiva (which contains leucocyte components, erythrocyte components, plasma and the like), or the like can be mentioned. It is to be noted that the term "gingival sulcus" generally means a crevice as a boundary between a tooth and the gingiva in the dental tissue.

(1) Gingival Sulcus Insert Section 11

The probe 1 for detecting a substance in the body according to the present application firstly has a gingival sulcus insert section 11 which can be inserted into the gingival sulcus. Insofar as the gingival sulcus insert section 11 can be inserted into the gingival sulcus, no particular limitation is imposed on its shape or size so that the gingival sulcus insert section 11 can be freely designed to meet its purpose. For example, its cross-sectional shape is not limited to such a circular shape as shown with respect to the first embodiment, but as illustrated in FIGS. 2B through 2F, its cross-sectional shape can also be designed into shapes such as oval, square, rectangle, crescent and the like.

Although not specifically shown in any figure, the gingival sulcus insert section 11 can be designed in a tapered shape such that its diameter or cross-sectional area gradually increases from its tip toward its main body. The designing into such a tapered shape can facilitate its insertion work into the gingival sulcus, and moreover, can avoid causing damage to the subject's gingiva.

The size of the gingival sulcus insert section 11 can be designed as desired insofar as the gingival sulcus insert section 11 can be inserted into the gingival sulcus. As the gingival sulcus of a normal subject is approx. 0.2 mm in width and approx. 2 mm in depth, it is preferred to set the short side or minor axis (see sign L in FIGS. 2A through 2F) of the gingival sulcus insert section 11 at 0.2 mm or smaller. The setting of the short side or minor axis of the gingival sulcus insert section 11 at 0.2 mm or smaller makes it possible to avoid causing irritation or damage to the gingiva when the gingival sulcus insert section 11 is inserted into the gingival sulcus.

Insofar as the gingival sulcus insert section 11 can be inserted into the gingival sulcus, no particular limitation is imposed on the material to be used for the gingival sulcus insert section 11. It is, however, preferred to use a material that has flexibility. The formation of the gingival sulcus insert section 11 with a material having flexibility makes it possible to avoid damage to the subject's gingiva. Examples of the material having flexibility can include resins, metals, ceramics, paper, fabrics such as felt materials, and the like.

Insofar as the probe 1 for detecting a substance in the body according to the present application can be connected to a meter for detecting a substance in the body, no particular limitations are imposed on the shapes, sizes and the like of portions of the probe 1 for detecting a substance in the body, said portions being other than the gingival sulcus insert section 11, and therefore, the shapes, sizes and the like of such portions of the probe 1 for detecting a substance in the body can be designed as desired depending on the purpose. When optical fibers are used as will be mentioned below, for example, optical detection can be realized as shown in the second embodiment of FIG. 3, specifically by forming a main body with a ferrule (optical connecting member) F1 and a sleeve S and connecting the ferrule F1 and another ferrule F2 on the side of the meter via the sleeve S. It is to be noted that signs OF1 and OF2 indicate optical fibers, respectively.

In the second embodiment, the sleeve S is arranged on the side of a probe 1 for detecting a substance in the body according to the present application. It is, however, to be noted that the present application is not limited to this embodiment and that it is free to design such that the ferrule F2 on the side of the meter may be provided with the sleeve S or the sleeve S may be used only when connecting the ferrules F1 and F2 together.

(2) Sensitive Part 12

The gingival sulcus insert section 11 is provided with a sensitive part 12. Included in this sensitive part 12 is or are one or more detection substances that permit optical detection of a substance in the body based on an interaction with the substance in the body.

Insofar as the above-described detection substance or substances can be incorporated in the sensitive part 12, no particular limitation is imposed on the manner of formation of the sensitive part 12, and therefore, the sensitive part 12 can be formed in a desired manner. For example, the sensitive part 12 can be formed with the above-described detection substance or substances immobilized directly on the gingival sulcus insert section 11 by coating a solution, which contains the above-described detection substance or substances optionally in combination with one or more other substances, onto the gingival sulcus insert section 11 at a desired position thereof and then subjecting the coated solution to immobilization reaction or reactions, drying and the like.

As an alternative, the sensitive part 12 can also be formed by immobilizing the above-described detection substance or substances in a film making use of a material that gives no adverse effect to the body. Described more specifically, a sensitive part in the form of a film with the above-described detection substance or substances immobilized therein (hereinafter called "the sensitive film") can be formed on the gingival sulcus insert section 11, for example, by mixing a solution, which contains the above-described detection substance or substances, and another solution, which contains a material capable of forming the film, with each other, coating the resulting mixture onto the gingival sulcus insert section 11 at a desired position thereof, and then conducting drying, light irradiation and the like.

In this case, no particular limitation is imposed on the material for forming the sensitive film and a known material can be chosen and used as desired, insofar as it is a material that can immobilize the above-described detection substance or substances and gives no adverse effect to the body. Usable examples can include UV-curable resins, thermosetting resins, agarose gel, polyacrylamide gel, glutaraldehyde, other porous immobilizing materials, commonly-employed enzyme-immobilizing agents, and the like.

Desired one of these materials can be chosen depending on the kind or kinds, properties and the like of the detection substance or substances to be immobilized. When it is desired to incorporate, for example, one or more enzymes in the sensitive part 12 as will be described subsequently herein, it is preferred to choose a UV-curable resin or the like such that its or their enzymatic activity will not be impaired.

The probe 1 for detecting a substance in the body according to the present application can detect a substance in the body in real time by using a meter or the like that can optically perform detection of the substance in the body.

Theoretically, it is also possible to perform electrochemical measurement of a substance in the body in real time by using an electrochemical sensor or the like and inserting its electrodes directly into the gingival sulcus. When such an electrochemical sensor or the like is used, however, salt components in gingival crevicular fluid deposit on the electrodes of the sensor used in the measurement, leading to variations in measurement value. It is, therefore, difficult to obtain test values of accuracy high enough to withstand a medical diagnosis. Moreover, the sensor is prone to damage due to the salt components in the gingival crevicular fluid, and therefore, the electrochemical measurement is costly and can be hardly applied for continuous measurement.

In the probe 1 for detecting a substance in the body according to the present application, however, one or more substances that permit optical detection of a substance in the body are incorporated in the sensitive part 12. Therefore, the optical detection of the target substance in the body is feasible, thereby making it possible to obtain a measurement value of high accuracy.

No particular limitation is imposed on the one or more detection substances to be incorporated in the sensitive part 12, insofar as it permits or they permit the optical detection of a substance in the body through an interaction, chemical reaction, enzyme reaction or the like with the substance in the body. Depending on the substance in the body as the target of the detection, one or more detection substances can be chosen and used as desired.

The substance in the body which is the target of the detection is one that can be used for an analysis or diagnosis in various fields. Saccharides, purine derivatives, glycolytic products, amino acids, lipids and the like, such as those to be described hereinafter, can serve as important indices of lifestyle-related diseases, such as diabetes, dyslipidemia and hyperuricemia, and other metabolic disorders especially in medical fields. They can also serve as indices for the prevention, alleviation and treatment of diseases associated with the above-mentioned diseases, for example, a broad range of diseases such as arterial sclerosis, cerebral infarction, subarachnoid hemorrhage, heart diseases such as heart failure, and cerebrovascular diseases. Such substances in the body may desirably be subjected to long-term monitoring at constant intervals, or in some instances, every predetermined time from the standpoint of health control or checking any change in symptom. In an invasive measuring method such as the collection of blood, however, such long-term monitoring is difficult due to a burden or the like on the subject. In contrast, the present application permits noninvasive measurement, and therefore, facilitates long-term monitoring at constant intervals or, if necessary, every predetermined time. Moreover, the present application can noninvasively and conveniently perform measurement, and therefore, can be used not only in medical fields but also in a wide range of fields such as crime lab work.

A description will hereinafter be made by exemplifying substances in the body as detection targets and giving examples of detection substances suited for the substances in the body.

(2-1) Where the Substance in the Body is a Saccharide

Examples of the saccharide can include monosaccharides such as ribose, glucose, galactose and fructose, and disaccharides such as lactose and sucrose.

As mentioned above, it is known, for example, that the glucose level in gingival crevicular fluid changes with time in substantial conformity with the glucose level in blood. It is, therefore, possible to perform the diagnosis, treatment or control of diabetes or hyperglycemia by measuring the glucose level in gingival crevicular fluid.

(2-1-1) Boronic Acid Compound

A boronic acid compound specifically binds to a saccharide to form a saccharide-baronage complex. By incorporating this boronic acid compound in the sensitive part 12 and inserting the gingival sulcus insert section 11 of the probe 1 for detecting a substance in the body according to the present application into the gingival sulcus, a saccharide (for example, D-glucose) in gingival crevicular fluid and the boronic acid compound incorporated in the sensitive part 12 bind to each other.

When the boronic acid compound (for example, phenylboronic acid compound) specifically binds to the saccharide to form the saccharide-boronate complex (see the below-described chemical reaction formula (1)), the intensity of fluorescence from the boronic acid compound changes. The glucose level in the gingival crevicular fluid can, therefore, be determined by measuring a change in the intensity of fluorescence from the sensitive part 12 of the probe 1 for detecting a substance in the body according to the present application.

Saccharide+boronic acid compound→saccharide-boronate complex (1)

(2-1-2) Substance in the Body: Glucose/Detection Substances: Glucose Oxidase, Peroxidase, and 10-acetyl-3,7-dihydroxyphenoxazine (ADHP)

Glucose oxidase catalyzes a reaction that forms D-glucono-1,5-lactone and hydrogen peroxide from D-glucose (see the below-described chemical reaction formula (2)).

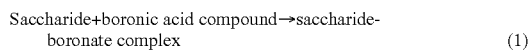

(2)

D-glucose + O₂ —glucose oxidase→ D-glucose-1,5-lactone + H₂O₂

In the presence of peroxidase, hydrogen peroxide converts 10-acetyl-3,7-dihydroxyphenoxazine (ADHP) into resorufin. ADHP does not emit fluorescence, but by its conversion into resorufin, fluorescence is emitted (see the below-described chemical reaction formula (3)). Therefore, this resorufin functions as a fluorescence source for optical detection.

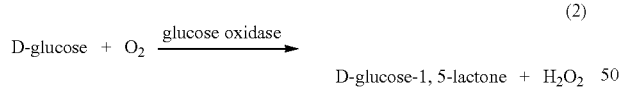

(3)

H₂O₂ + ADHP —peroxidase→ resorufin + CH₃COOH + H₂O
(fluorescence source)

When this reaction principle is used, the incorporation of glucose oxidase, peroxidase and ADHP in the sensitive part 12 allows the above-described series of reactions to proceed by glucose in gingival crevicular fluid upon insertion of the gingival sulcus insert section 11 of the probe 1 for detecting a substance in the body according to the present application into the gingiva. The glucose level in the gingival crevicular fluid can then be determined by measuring the intensity of fluorescence available from the sensitive part 12 of the probe 1 for detecting a substance in the body according to the present application.

By incorporating in the sensitive part 12 one or more first enzymes (for example, an oxidase and/or the like) for catalyzing a reaction in which a substance in the body in gingival crevicular fluid takes part, one or more second enzymes (for example, peroxidase) for catalyzing a reaction in which a product (for example, hydrogen peroxide) formed from the substance in the body through the catalytic reaction by the first enzyme or enzymes takes part, and one or more substances (for example, ADHP) from which fluorescence is emitted as a result of the catalytic reaction by the second enzyme or enzymes, the use of the probe 1 for detecting a substance in the body according to the present application makes it possible to perform optical detection of the substance in the body in the gingival crevicular fluid.

Examples of the oxidase can include glucose oxidase, alcohol oxidase, uricase (urate oxidase), lactate oxidase, fructosyl-amino acid oxidase, sarcosine oxidase, cholesterol oxidase, and the like. These oxidases can be used either singly or in combination depending on the substance in the body.

Before the treatment of the substance in the body with the first enzyme or enzymes, the substance in the body may be treated with a pretreatment enzyme to facilitate the reaction by the first enzyme or enzymes. The pretreatment enzyme can be a hydrolytic enzyme or the like. Examples of the hydrolytic enzyme can include protease, creatinase, creatininase, cholesterol esterase, and the like. They can be used either singly or in combination.

It is to be noted that instead of ADHP, o-dianisidine may be incorporated. When o-dianisidine is incorporated instead of ADHP in the reactive part 12, this o-dianisidine is oxidized with hydrogen peroxide (see the below-described chemical reaction (4)). As a result of the oxidation, the absorbance changes. Measurement of this change based on an absorption spectrum by visible light spectroscopy makes it possible to detect the substance in the body in the gingival crevicular fluid.

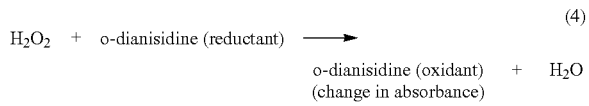

(4)

H₂O₂ + o-dianisidine (reductant) → o-dianisidine (oxidant) + H₂O
(change in absorbance)

(2-2) Where the Substance in the Body is an Alcohol

If the alcohol level in gingival crevicular fluid can be detected, the alcohol concentration can be more accurately measured not only in medical fields but also in fields such as, for example, drunk driving checks and alcohol-related measures at work although it has heretofore been a common practice to detect such an alcohol concentration from breath.

(2-2-1) Substance in the Body: Alcohol/Detection Substances: Alcohol Oxidase, Peroxidase, and 10-acetyl-3,7-dihydroxyphenoxazine (ADHP)

Alcohol oxidase is an oxidoreductase that catalyzes a reaction that alcohol is converted into aldehyde. In this reaction, hydrogen peroxide is produced with aldehyde (see the below-described chemical reaction formula (5)).

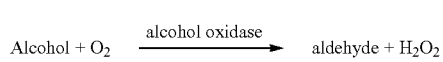
$$\text{Alcohol} + O_2 \xrightarrow{\text{alcohol oxidase}} \text{aldehyde} + H_2O_2 \quad (5)$$

In the presence of peroxidase, hydrogen peroxide converts 10-acetyl-3,7-dihydroxyphenoxazine (ADHP) into resorufin. ADHP does not emit fluorescence, but by its conversion into resorufin, fluorescence is emitted (see the above-described chemical reaction formula (3)). Therefore, this resorufin functions as a fluorescence source for optical detection.

When such a reaction principle is used, the incorporation of alcohol oxidase, peroxidase and ADHP in the sensitive part 12 allows the above-described series of reactions to proceed by the alcohol in gingival crevicular fluid upon insertion of the gingival sulcus insert section 11 of the probe 1 for detecting a substance in the body according to the present application into the gingiva. The alcohol level in the gingival crevicular fluid can then be determined by measuring the intensity of fluorescence emitted from the sensitive part 12 of the probe 1 for detecting a substance in the body according to the present application.

In the case of this reaction system, it is also possible to incorporate o-dianisidine instead of ADHP. When o-dianisidine is incorporated instead of ADHP in the reactive part 12, this o-dianisidine is oxidized with hydrogen peroxide (see the above-described chemical reaction (4)). As a result of the oxidation, the absorbance changes. Measurement of this change based on an absorption spectrum by visible light spectroscopy makes it possible to detect the alcohol in the gingival crevicular fluid.

(2-3) Where the Substance in the Body is a Purine Derivative

Examples of the purine derivatives can include purine, adenine, guanine, hypoxanthine, xanthine, theobromine, caffeine, uric acid, isoguanine, and the like.

If it is possible to more accurately measure, for example, the uric acid level in gingival crevicular fluid, the measurement value can be used for the diagnosis or the like of gout that exhibits hyperuricemia, hypouricemia, Lesch-Nyhan syndrome or the like.

(2-3-1) Substance in the Body: Uric Acid/Detection Substances: Uricase (Urate Oxidase), Peroxidase, and 10-acetyl-3,7-dihydroxyphenoxazine (ADHP)

Uricase is an enzyme that catalyzes a reaction represented by the following chemical reaction formula (6), and oxygen peroxide is also produced in the reaction.

$$\text{Uric acid} + O_2 \xrightarrow{\text{uricase}} \text{5-hydroxyiso uric acid} + H_2O_2 \quad (6)$$

In the presence of peroxidase, hydrogen peroxide converts 10-acetyl-3,7-dihydroxyphenoxazine (ADHP) into resorufin. ADHP does not emit fluorescence, but by its conversion into resorufin, fluorescence is emitted (see the above-described chemical reaction formula (3)). Therefore, this resorufin functions as a fluorescence source for optical detection.

When this reaction principle is used, the incorporation of uricase, peroxidase and ADHP in the sensitive part 12 allows the above-described series of reactions to proceed by uric acid in gingival crevicular fluid upon insertion of the gingival sulcus insert section 11 of the probe 1 for detecting a substance in the body according to the present application into the gingiva. The uric acid level in the gingival crevicular fluid can then be determined by measuring the intensity of fluorescence emitted from the sensitive part 12 of the probe 1 for detecting a substance in the body according to the present application.

It is to be noted that instead of ADHP, o-dianisidine may be incorporated. When o-dianisidine is incorporated instead of ADHP in the reactive part 12, this o-dianisidine is oxidized with hydrogen peroxide (see the above-described chemical reaction (4)). As a result of the oxidation, the absorbance changes. Measurement of this change based on an absorption spectrum by visible light spectroscopy makes it possible to measure the uric acid level in the gingival crevicular fluid.

(2-4) Where the Substance in the Body is a Glycolytic Product

Examples of the glycolytic product can include organic acids such as pyruvic acid and lactic acid.

If it is possible to more accurately measure, for example, lactic acid in gingival crevicular fluid, the measurement value can be used for the diagnosis, prevention or the like of lactic acidosis, mitochondrial disorder, hepatic function failure, lactic dehydrogenase deficiency, an oxygen-deficient condition of a tissue, diabetes, or the like.

(2-4-1) Substance in the Body: Lactic Acid/Detection Substances: Lactate Oxidase, Peroxidase, and 10-acetyl-3,7-dihydroxyphenoxazine (ADHP)

Lactate oxidase is an enzyme that catalyzes a reaction represented by the following chemical reaction formula (7), and oxygen peroxide is also produced in the reaction.

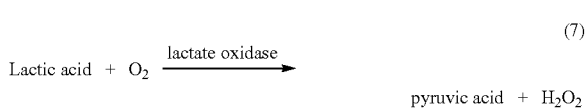
$$\text{Lactic acid} + O_2 \xrightarrow{\text{lactate oxidase}} \text{pyruvic acid} + H_2O_2 \quad (7)$$

In the presence of peroxidase, hydrogen peroxide converts 10-acetyl-3,7-dihydroxyphenoxazine (ADHP) into resorufin. ADHP does not emit fluorescence, but by its conversion into resorufin, fluorescence is emitted (see the above-described chemical reaction formula (3)). Therefore, this resorufin functions as a fluorescence source for optical detection.

When this reaction principle is used, the incorporation of lactate oxidase, peroxidase and ADHP in the sensitive part 12 allows the above-described series of reactions to proceed by lactic acid in gingival crevicular fluid upon insertion of the gingival sulcus insert section 11 of the probe 1 for detecting a substance in the body according to the present application into the gingiva. The uric acid level in the gingival crevicular fluid can then be determined by measuring the intensity of fluorescence emitted from the sensitive part 12 of the probe 1 for detecting a substance in the body according to the present application.

It is to be noted that instead of ADHP, o-dianisidine may be incorporated. When o-dianisidine is incorporated instead of ADHP in the reactive part 12, this o-dianisidine is oxidized with hydrogen peroxide (see the above-described chemical reaction (4)). As a result of the oxidation, the absorbance changes. Measurement of this change based on an absorption spectrum by visible light spectroscopy makes it possible to measure the lactic acid level in the gingival crevicular fluid.

(2-5) Where the Substance in the Body is a Glycated Protein

Examples of the glycated protein can include fructosamine, glycated hemoglobin, glycated albumin, and the like.

If it is possible to more accurately measure, for example, fructosamine, glycated hemoglobin or glycated albumin in gingival crevicular fluid, the measurement value can be used for the diagnosis, prevention or the like of diabetes, hyperglycemia or the like.

(2-5-1) Substance in the Body: Glycated Albumin or Albumin/Detection Substances: Protease, Fructosyl-Amino Acid Oxidase, Peroxidase, and 10-acetyl-3,7-dihydroxyphenoxazine (ADHP)

(2-5-2) Substance in the Body: Glycated Albumin or Albumin/Detection Substances: Component (A): Protease, and Components (B): Fructosyl-Amino Acid Oxidase, Peroxidase, and 10-acetyl-3,7-dihydroxyphenoxazine (ADHP)

Protease is a protein-degrading enzyme that catalyzes a reaction represented by the following reaction formula (8), and upon degradation of a protein into an amino acid, liberates a glycosylated amino acid.

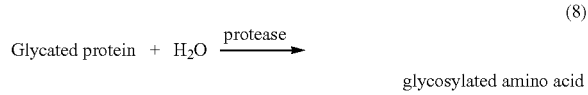

(8)

Fructosyl-amino acid oxidase is an enzyme that catalyzes a reaction represented by the following chemical reaction formula (9), and oxygen peroxide is also produced in the reaction.

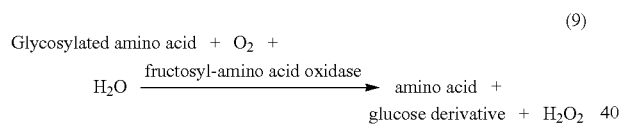

(9)

Peroxide converts 10-acetyl-3,7-dihydroxyphenoxazine (ADHP) into resorufin. ADHP does not emit fluorescence, but by its conversion into resorufin, fluorescence is emitted (see the above-described chemical reaction formula (3)). Therefore, this resorufin functions as a fluorescence source for optical detection.

When this reaction principle is used, the incorporation of protease, fructosyl-amino acid oxidase, peroxidase and ADHP in the sensitive part 12 allows the above-described series of reactions to proceed by a glycated protein in gingival crevicular fluid upon insertion of the gingival sulcus insert section 11 of the probe 1 for detecting a substance in the body according to the present application into the gingiva. The glucose level can be determined from the amount of glucose bonded to the glycated protein in the gingival crevicular fluid by measuring the intensity of fluorescence emitted from the sensitive part 12 of the probe 1 for detecting a substance in the body according to the present application. It is to be noted that, because protease is a protein-degrading enzyme and tends to affect other enzymes, protease may suitably be incorporated in a sensitive part other than the sensitive part 12 in which fructosyl-amino acid oxidase, peroxidase and ADHP are incorporated.

It is to be noted that instead of ADHP, o-dianisidine may be incorporated. When o-dianisidine is incorporated instead of ADHP in the reactive part 12, this o-dianisidine is oxidized with hydrogen peroxide (see the above-described chemical reaction (4)). As a result of the oxidation, the absorbance changes. Measurement of this change based on an absorption spectrum by visible light spectroscopy makes it possible to measure the glucose level from the amount of glucose bonded to the glycated protein in the gingival crevicular fluid.

(2-6) Where the Substance in the Body is an Amino Acid

Examples of the amino acid can include creatinine, creatine, glutamic acid, and the like.

If it is possible to more accurately measure, for example, creatinine or creatine in gingival crevicular fluid, the measurement value can be used for the diagnosis, prevention or the like of renal function disorder or the like. As the creatinine concentration rises upon occurrence of a loss of renal function, the creatinine concentration can serve as an index of renal function.

(2-6-1) Substance in the Body: Creatinine or Creatine/Detection Substances: Creatininase, Creatinase, Sarcosine Oxidase, Peroxidase, and 10-acetyl-3,7-dihydroxyphenoxazine (ADHP)

(2-6-2) Substance in the Body: Creatinine or Creatine/Detection Substances: Creatinase, Sarcosine Oxidase, Peroxidase, and 10-acetyl-3,7-dihydroxyphenoxazine (ADHP)

Creatininase catalyzes a reaction represented by the following chemical reaction formula (10).

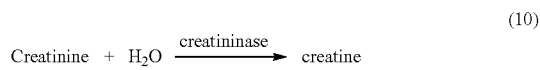

(10)

Creatinase catalyzes a reaction represented by the following chemical reaction formula (11).

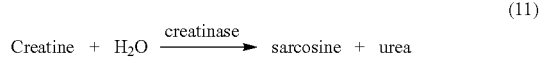

(11)

Sarcosine oxidase is an enzyme that catalyzes a reaction represented by the following chemical reaction formula (12), and oxygen peroxide is also produced in the reaction.

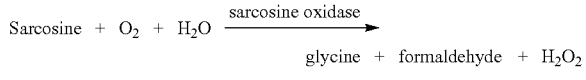

(12)

In the presence of peroxidase, hydrogen peroxide converts 10-acetyl-3,7-dihydroxyphenoxazine (ADHP) into resorufin. ADHP does not emit fluorescence, but by its conversion into resorufin, fluorescence is emitted (see the above-described chemical reaction formula (3)). Therefore, this resorufin functions as a fluorescence source for optical detection.

When this reaction principle is used, the incorporation of creatinase, sarcosine oxidase, peroxidase and ADHP, and optionally, creatininase in the sensitive part 12 allows the above-described series of reactions to proceed by creatine and creatinine in gingival crevicular fluid upon insertion of the gingival sulcus insert section 11 of the probe 1 for detecting a substance in the body according to the present application into the gingiva. The creatine concentration and creatinine concentration in the gingival crevicular fluid can then be determined by measuring the intensity of fluorescence emitted from the sensitive part 12 of the probe 1 for detecting a substance in the body according to the present application. It is to be noted that creatininase may be omitted when creatine is to be detected. When creatinine is to be detected, on the other hand, the additional incorporation of creatininase in the sensitive part 12 is desired to increase the accuracy of detection of creatinine.

It is to be noted that instead of ADHP, o-dianisidine may be incorporated. When o-dianisidine is incorporated instead of ADHP in the reactive part 12, this o-dianisidine is oxidized with hydrogen peroxide (see the above-described chemical reaction (4)). As a result of the oxidation, the absorbance changes. Measurement of this change based on an absorption spectrum by visible light spectroscopy makes it possible to measure the creatine concentration or creatinine concentration in the gingival crevicular fluid.

The concentration of a D- or L-amino acid in gingival crevicular fluid can also be measured when D- or L-amino acid oxidase, peroxidase and ADHP are incorporated in the sensitive part 12. It is to be noted that the (D- or L-)amino acid oxidase produces hydrogen peroxide together with ammonia from the D- or L-amino acid.

(2-7) Where the Substance in the Body is a Lipid

Examples of the lipid can include cholesterol, cholesteryl esters, triglyceride (neutral fat), phospholipids, free fatty acids, and the like.

If it is possible to more accurately measure, for example, cholesterol or a cholesteryl ester in gingival crevicular fluid, the measurement value can be used for the diagnosis, prevention or the like of abnormal lipid metabolism or the like. Total cholesterol value can serve as an index of hypercholesteremia or hyperlipemia.

(2-7-1) Substance in the Body: Cholesterol or Cholesteryl Ester/Detection Substances: Cholesterol Esterase, Cholesterol Oxidase, Peroxidase, and 10-acetyl-3,7-dihydroxyphenoxazine (ADHP)

(2-7-2) Substance in the Body: Cholesterol or Cholesteryl Ester/Detection Substances: Cholesterol Oxidase, Peroxidase, and 10-acetyl-3,7-dihydroxyphenoxazine (ADHP)

Cholesterol esterase (cholesteryl esterase, sterol ester) catalyzes a reaction represented by the following chemical reaction formula (13).

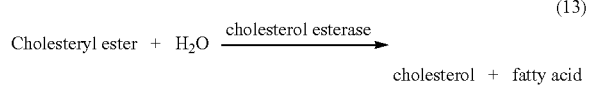

(13)

Cholesterol oxidase is an enzyme that catalyzes a reaction represented by the following chemical reaction formula (14), and oxygen peroxide is also produced in the reaction.

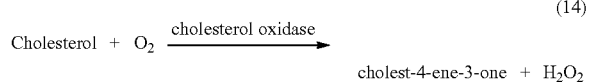

(14)

In the presence of peroxidase, hydrogen peroxide converts 10-acetyl-3,7-dihydroxyphenoxazine (ADHP) into resorufin. ADHP does not emit fluorescence, but by its conversion into resorufin, fluorescence is emitted (see the above-described chemical reaction formula (3)). Therefore, this resorufin functions as a fluorescence source for optical detection.

When this reaction principle is used, the incorporation of cholesterol oxidase, peroxidase and ADHP, and optionally, cholesterol esterase in the sensitive part 12 allows the above-described series of reactions to proceed by cholesterol and the cholesterol ester in gingival crevicular fluid upon insertion of the gingival sulcus insert section 11 of the probe 1 for detecting a substance in the body according to the present application into the gingiva. The cholesterol level or total cholesterol level in the gingival crevicular fluid can then be determined by measuring the intensity of fluorescence emitted from the sensitive part 12 of the probe 1 for detecting a substance in the body according to the present application. It is to be noted that upon measurement of the total cholesterol level, cholesterol esterase is also incorporated in the sensitive part 12. This additional incorporation of cholesterol esterase increases the accuracy of detection of the total cholesterol level, and therefore, is desired.

It is to be noted that instead of ADHP, o-dianisidine may be incorporated. When o-dianisidine is incorporated instead of ADHP in the reactive part 12, this o-dianisidine is oxidized with hydrogen peroxide (see the above-described chemical reaction (4)). As a result of the oxidation, the absorbance changes. Measurement of this change based on an absorption spectrum by visible light spectroscopy makes it possible to measure the cholesterol level or the total cholesterol level in the gingival crevicular fluid.

(2-8) Other Candidate Examples of the Substance in the Body

It is to be noted that in the present application, the substance in the body as a target of detection is not limited to the above-mentioned ones and that a variety of substances in the body can be detected by changing the enzyme or enzymes to be incorporated in the sensitive part 12.

Illustrative can be the activity of aspartic acid aminotransferase (AST) and that of alanine aminotransferase (ALT). They are parameters of liver function.

Insofar as the above-described sensitive part 12 is arranged on the gingival sulcus insert section 11, no particular limitation is imposed on its shape so that its shape can be designed as desired. Taking as an example a case in which an optical fiber is used, one embodiment of the sensitive part 12 will be described hereinafter.

Figure 4:
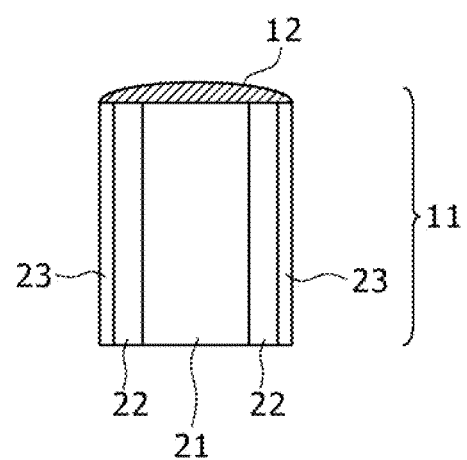
FIG. 4 is a schematic cross-sectional diagram of a gingival sulcus insert section in a third embodiment of the probe for detecting a substance in the body according to the present application as viewed from the side.

FIG. 4 is a schematic cross-sectional view of a gingival sulcus insert section 11 of a probe 1 for detecting a substance in the body according to the present application as viewed from the side. As shown in FIG. 4, the sensitive part 12 can be arranged on a cut end face of an optical fiber such that the sensitive part 12 extends over all of a core 21, a cladding 22 and a coating 23.

Figure 5:
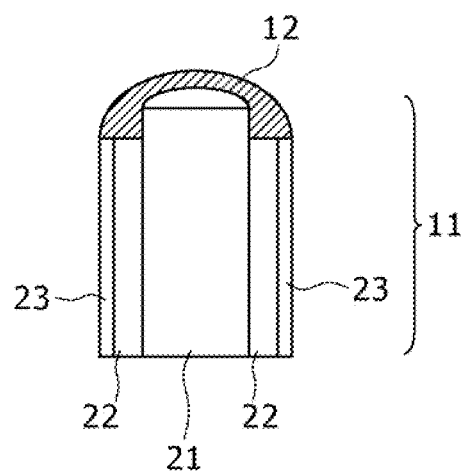
FIG. 5 is a schematic cross-sectional diagram of a gingival sulcus insert section in a fourth embodiment of the probe for detecting a substance in the body according to the present application as viewed from the side.
Figure 6:
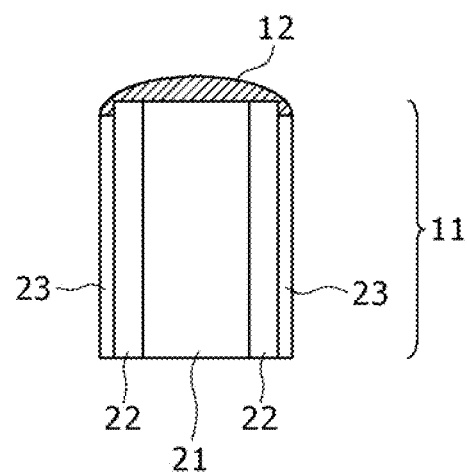
FIG. 6 is a schematic cross-sectional diagram of a gingival sulcus insert section in a fifth embodiment of the probe for detecting a substance in the body according to the present application as viewed from the side.
Figure 7:
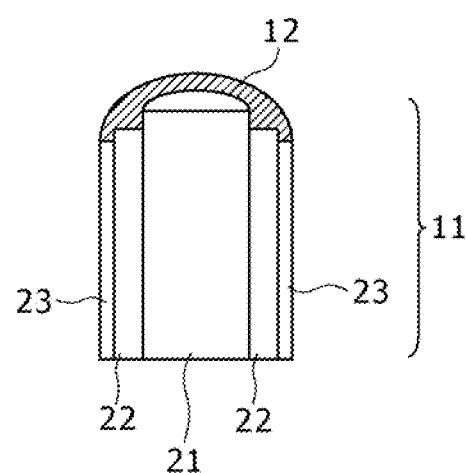
FIG. 7 is a schematic cross-sectional diagram of a gingival sulcus insert section in a sixth embodiment of the probe for detecting a substance in the body according to the present application as viewed from the side.

An optical fiber can be cut beforehand with only a core 21 extending out from the surrounding as depicted in FIG. 5 or with a core 21 and a cladding 22 extending out from the surrounding as depicted in FIG. 6. A sensitive part 21 can then be arranged such that it extends over all of the core 21, the cladding 22 and a coating 23. As illustrated in FIG. 7, a core 21, a cladding 22 and a coating 23 can be cut stepwise (in steps) beforehand as a further alternative, and a sensitive part 12 can then be arranged such that it extends over all of the core 21, cladding 22 and coating 23. By arranging the sensitive part 12 in such a manner as described above, the sensitive part 12 can be arranged in a more firm state on the cut end face of the optical fiber.

Figure 8:
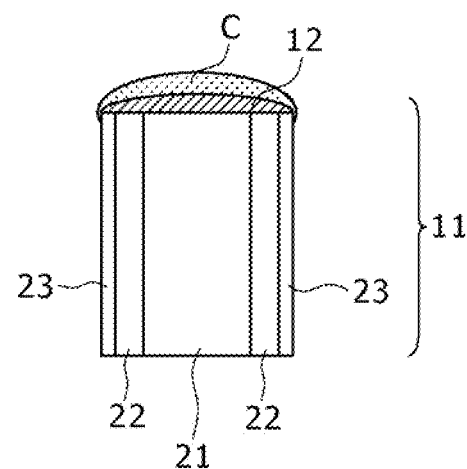
FIG. 8 is a schematic cross-sectional diagram of a gingival sulcus insert section in a seventh embodiment of the probe for detecting a substance in the body according to the present application as viewed from the side.

As a still further alternative, a coating layer C can be arranged over a surface of the sensitive part 12, for example, as shown in FIG. 8. The arrangement of the coating layer C as described above makes it possible to arrange the sensitive part 12 in a still more firm state and also to reduce damage to the gingiva. It is also possible to protect the substance or substances incorporated in the sensitive part 12. Even when a substance which affects the body is incorporated in the sensitive part 12, for example, the probe 1 for detecting a substance in the body according to the present application can still be used safely.

As the material to be used for the coating layer C, it is possible to use one having no adverse effect for the body. Such a material can be chosen and used as desired. Use of a naturally-occurring material such as, for example, agar gel (agarose) permits safer use of the probe 1 for detecting a substance in the body according to the present application.

It is to be noted that FIG. 8 shows an example similar to the embodiment illustrated in FIG. 4 except that the sensitive part 12 is coated. The coated sensitive part is not limited to the example of FIG. 8, and in each of the embodiments shown in FIGS. 5 to 7, the sensitive part 12 can be coated.

Insofar as the sensitive part 12 can be inserted into the gingival sulcus, no particular limitation is imposed on its shape, and the shape of the sensitive part 12 can be designed as desired. For example, the sensitive part 12 can be designed in an obliquely cut shape or a cone shape to facilitate its insertion into the gingival sulcus.

(3) Optical Waveguide 13

In the sensitive part 12 of the probe 1 for detecting a substance in the body according to the present application, one or more detection substances that permit optical detection of a substance in the body are immobilized. The substance in the body in gingival crevicular fluid can, therefore, be detected substantially in real time by promptly subjecting the probe 1 for detecting a substance in the body to optical detection after it is pulled out of the gingival sulcus.

It is also suitable to contrive such that the probe 1 for detecting a substance in the body according to the present application is provided with an optical waveguide 13 to perform the irradiation of light onto the sensitive part 12 and/or the detection of light from the sensitive part 12. The provision of such an optical waveguide makes it possible to detect the substance in the body in the gingival crevicular fluid with the probe 1 for detecting a substance in the body being kept inserted in the gingival sulcus. As the substance in the body in the gingival crevicular fluid can be detected with the probe for detecting a substance in the body being kept inserted in the gingival sulcus, time-course detection or measurement can be readily performed.

Insofar as the irradiation of light onto the sensitive part 12 and/or the transmission of optical information generated from the inside of the sensitive part 12 is feasible, no particular limitation is imposed on the manner of formation of the optical waveguide 13, and the optical waveguide can be designed as desired. The optical waveguide 13 can be formed, for example, from a rod, optical fiber or light guide plate.

Figure 3:
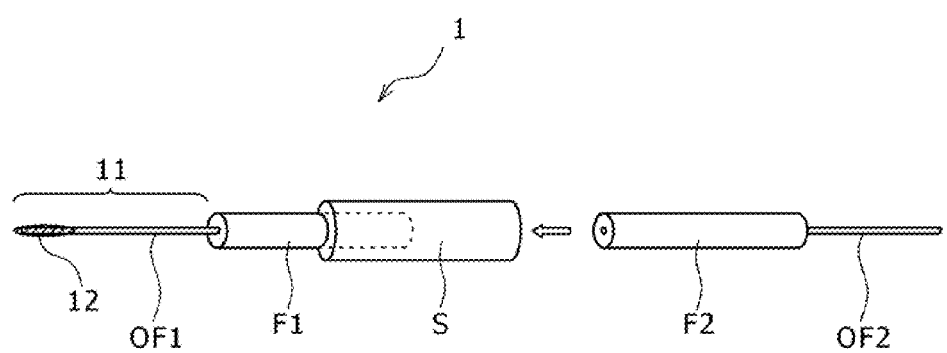
FIG. 3 is a schematic conceptual diagram illustrating a manner of connecting a second embodiment of the probe for detecting a substance in the body according to the present application to a meter for detecting a substance in the body.

Use of an optical waveguide 13, which makes use of an optical fiber as in the second embodiment shown in FIG. 3, as the gingival sulcus insert section 11 in the probe 1 for detecting a substance in the body according to the present application makes it possible to also use the gingival sulcus insert section 11 as an optical waveguide 13.

(4) Capillary Portion 14

Figure 9:
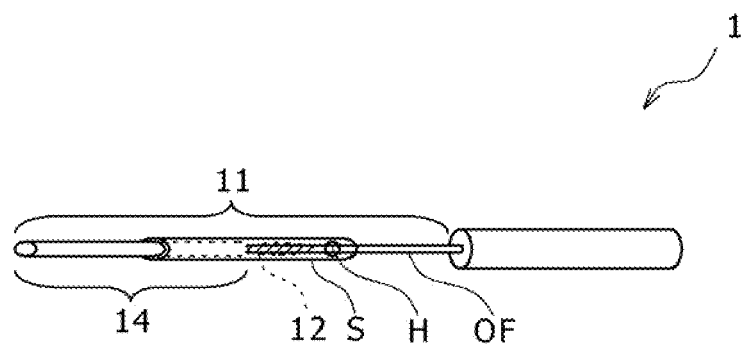
FIG. 9 is a schematic conceptual diagram of an eighth embodiment of the probe for detecting a substance in the body according to the present application.

With reference to FIG. 9, the eighth embodiment of the probe 1 for detecting a substance in the body according to the present application will be described next. In this embodiment, a capillary portion 14 is arranged as a tip portion of a gingival sulcus insert section 11. The arrangement of this capillary portion 14 makes it possible to collect gingival crevicular fluid under capillary action upon insertion of the gingival sulcus insert section 11 into the gingival sulcus. The gingival crevicular fluid so collected can be smoothly introduced into a sensitive part 12 via the capillary portion 14.

The arrangement of the capillary portion 14 can also improve the accuracy of measurement, because gingival crevicular fluid can be collected in a predetermined constant amount corresponding to the internal capacity of the capillary portion 14.

The size of the capillary portion 14 can be designed as desired, insofar as the capillary portion 14 can be inserted into the gingival sulcus and can collect gingival crevicular fluid under capillary action. Preferably, however, its outer diameter may be set at 500 µm or smaller. The setting of its outer diameter at 500 µm or smaller makes it possible to surely collect gingival crevicular fluid from the gingival sulcus and also to avoid causing irritation or damage to the gingiva when the capillary portion 14 is inserted into the gingival sulcus.

Figure 10:
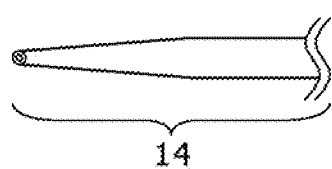
FIG. 10 is an enlarged, fragmentary, schematic, conceptual diagram of a capillary portion in a ninth embodiment of the probe for detecting a substance in the body according to the present application.

Like the ninth embodiment shown in FIG. 10, a capillary portion 14 can be designed in a tapered structure such that its diameter or cross-sectional area gradually increases from the tip of the capillary portion 14 toward the sensitive part 12 (see FIG. 9). The designing in such a tapered structure makes it possible to more easily perform the insertion of the capillary portion 14 into the gingival sulcus and also to more surely avoid causing damage to the subject's gingiva. In this case, the outer diameter of the tip of the tapered structure may preferably be set at 150 µm or smaller, because such an outer diameter can avoid causing irritation or damager to the gingiva when the capillary portion 14 is inserted into the gingival sulcus.

No particular limitation is imposed on the material to be used for the capillary portion 14, insofar as the capillary portion 14 can be inserted into the gingival sulcus. It is preferred to use a material having flexibility, because the formation of the gingival sulcus insert section 11 with the material having flexibility can effectively avoid causing damage to the subject's gingiva. Examples of the material having flexibility can include resins, paper, fabrics such as felt materials, and the like.

No particular limitation is imposed on the manner of the arrangement of the capillary portion 14 as a tip portion in the gingival sulcus insert section 11, insofar as gingival crevicular fluid collected through the capillary portion 14 can be introduced to the sensitive part 12. For example, the gingival sulcus insert section 11 and the capillary portion 14 may be simply kept in contact with each other, or may be adhered to each other with a curable resin or the like.

As shown in the eighth embodiment of FIG. 9, the gingival sulcus insert section 11 and the optical fiber OF, which functions as an optical waveguide 13, can be connected to the capillary portion 14 by using a cover such as the sleeve S. The use of such a cover can additionally bring about waterproof effect and dustproof effect for the interior of the probe 1 for detecting a substance in the body. For the adhesion between the sleeve S and the optical fiber OF and the adhesion between the sleeve S and the capillary portion 14 in the above-described case, it is preferred to use a filler such as a UV-curable resin, thermosetting resin, silicone resin or epoxy-based curing resin.

When the optical fiber OF and the capillary portion 14 are connected to each other via a cover like the sleeve S as described above, the sleeve S may preferably be provided with a vent hole H because this vent hole H functions as an air vent upon collecting gingival crevicular fluid under capillary action.

When the capillary portion 14 is arranged, no particular limitation is imposed on the position where the sensitive part 12 is to be formed. Like the eighth embodiment of FIG. 9, for example, the sensitive part 12 may be arranged at the position of connection between the optical fiber OF, which functions as an optical waveguide 13, and the capillary portion 14 in the gingival sulcus insert section 11.

Figure 11:
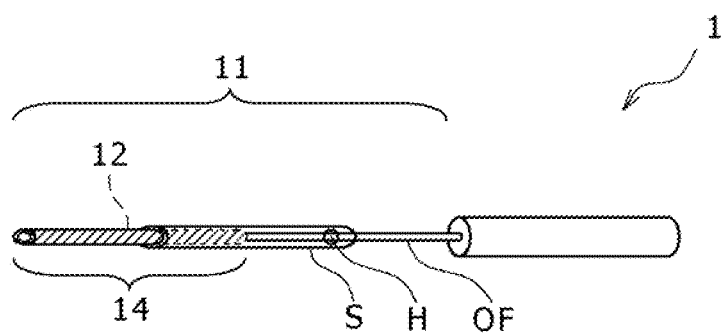
FIG. 11 is a schematic conceptual diagram of a tenth embodiment of the probe for detecting a substance in the body according to the present application.

Like the tenth embodiment of FIG. 11, a sensitive part 12 can be arranged on an inner wall of a capillary portion 14.

No limitation is imposed on the manner of formation of the sensitive part 12 on the inner wall of the capillary portion 14, and therefore, the capillary portion 14 can be formed in a desired manner. For example, the sensitive part 12 can be formed with the above-described detection substances immobilized directly on the inner wall of the capillary portion 14 by introducing a solution, which contains the above-described detection substances, into the capillary portion 14 under capillary action and then drying the thus-introduced solution.

As an alternative, the sensitive part 12 can also be formed by immobilizing the above-described detection substances in a film making use of a material that gives no adverse effect to the body. Described more specifically, a sensitive film can be formed with the above-described detection substances immobilized on the inner wall of the capillary portion 14, for example, by mixing a solution, which contains the above-described detection substances, and another solution, which contains the above-described immobilizing material, together, introducing the resulting mixture into the capillary portion 14 under capillary action, and then performing drying, light irradiation and the like.

For example, the detection substances can be immobilized by mixing them in an aqueous solution—which contains a water-soluble compound having one or more of various photoreactive groups, for example, a compound having one or more azido groups (—N3), specifically a diazide compound having two azido groups (e.g., a compound of a structure that two phenylazido groups are coupled together) and a water-soluble high-molecular resin, gel or compound—(an aqueous immobilizing solution), introducing and adhering the resulting aqueous solution mixture onto the inner wall of the capillary portion 14 under capillary action, drying off water, and then irradiating light (ultraviolet ray). In this manner, the detection substances can be surely immobilized on the inner wall of the capillary portion 14 without causing clogging of the capillary while controlling the volume of the sensitive part 12.

When azido groups are exposed to light, nitrogen molecules are liberated to form nitrogen radicals. These nitrogen radicals can bind not only to functional groups such as amino groups and carboxyl groups but also to carbon atoms making up an organic compound. Azido groups, therefore, have a property that they can form covalent bonds with most organic compounds.

The use of the capillary action available from the capillary portion 14 makes it possible to introduce a predetermined constant amount of the solution, which contains the detection substances, into the capillary portion 14 as described above. On the inner wall of the capillary portion 14, the sensitive part 12 can hence be arranged with the detection substances incorporated in predetermined constant amounts therein.

The inner wall of the capillary portion 14 may preferably be formed in a solid phase having hydrophilic groups such as alcoholic hydroxyl groups, because such a solid phase facilitates to arrange the sensitive part 12 on the inner wall of the capillary portion 14. Examples of such a solid phase can include glass, silica, polyol resins, surface-modified resins, solid phases with hydrophilic groups applied thereon by silane coupling agents or the like, and the like.

The inner wall of the capillary portion 14 may be nonporous or porous, with formation into a structure of an increased surface area being particularly preferred. The increased surface area makes it possible to incorporate the detection substances more in the sensitive part 12 to be provided on the surface.

Figure 12:
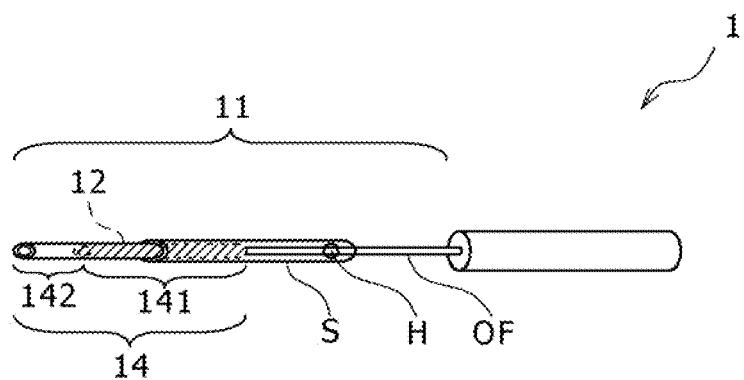
FIG. 12 is a schematic conceptual diagram of an eleventh embodiment of the probe for detecting a substance in the body according to the present application.

Referring next to FIG. 12, the eleventh embodiment of the probe 1 for detecting a substance in the body according to the present application will be described. In this embodiment, a sensitive part 12 is arranged on the inner wall of a capillary portion 14 at a position spaced a predetermined distance from a tip of the capillary portion 14. For example, the capillary portion 14 is provided with a capillary portion 142 and a capillary portion 141. The capillary portion 142 has no sensitive part and is arranged on the side of the tip of the capillary portion 14, while the capillary portion 141 has the sensitive part 12 and is connected to the capillary portion 142.

When the position of the sensitive part 12 is spaced the predetermined distance from the tip of the capillary portion 14 as described above, various reactions are allowed to take place with the detection substances in the sensitive part 12 as soon as the gingival crevicular fluid has been drawn up to a predetermined amount. It is, therefore, possible to stabilize the reactions between the substance in the body contained in the gingival crevicular fluid and the detection substances. As a consequence, detection and measurement of still higher accuracy can be performed.

No particular limitation is imposed on the manner of formation of the capillary portion 14 in the eleventh embodiment depicted in FIG. 12. For example, similar to the above-described tenth embodiment illustrated in FIG. 11, the capillary portion 14 can be easily formed by preparing the capillary portion 141 with the sensitive part 12 arranged on the entire inner wall thereof and then connecting it to the capillary portion 142 having no sensitive part.

As a modification of the above-described tenth or eleventh embodiment, plural sensitive parts 12 with different combinations of detection substances immobilized therein may be formed on the inner wall of the capillary portion 14.

Using the capillary action available from the capillary portion 14, for example, a solution containing one of the above-described combinations of detection substances is introduced onto one side of the inner wall of the capillary portion 14 from the corresponding one side of the tip of the capillary portion 14. From the opposite side of the tip of the capillary portion 14, a solution containing the other combination of detection substances (including, for example, a different enzyme) is introduced onto the corresponding opposite side of the inner wall. By immobilizing these detection substances on the inner wall of the capillary portion 14, plural sensitive parts (sensitive films) 12 can be formed both extending along a longitudinal direction.

As an alternative, the solution containing the one combination of detection substances is introduced from one end of the capillary portion 14 onto the inner wall on the side of the one end. On the other hand, the solution containing the other combination of detection substances (including, for example, the different enzyme) is introduced from the opposite end of the capillary portion 14 onto the inner wall on the side of the opposite end. By immobilizing these different combinations of detection substances on the inner wall of the capillary portion 14, respectively, a plurality of sensitive parts (sensitive films) 12 can be formed in cylindrical forms.

In the manner described above, plural detection substances can be provided for the detection of a substance in the body, and can be suitably immobilized on the inner wall at different positions, respectively. It is, therefore, possible to suppress inhibition or competition between the detection substances themselves. As a consequence, detection or the like of still higher accuracy can be performed.

Figure 13:
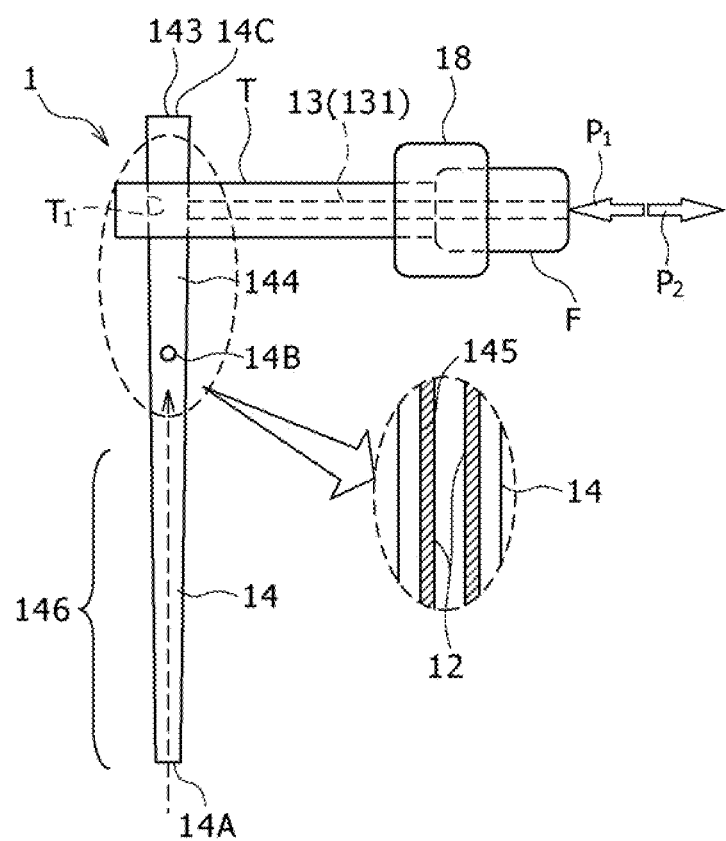
FIG. 13 is a schematic conceptual diagram illustrating the basic construction of an embodiment in which an optical waveguide is connected to a cylindrical side wall of a capillary portion that makes up the probe for detecting a substance in the body according to the present application.

With reference to FIG. 13, one example of modified embodiments of the probe 1 for detecting a substance in the body according to the present application will be described next. Specifically, FIG. 13 depicts the basic construction of an embodiment in which an optical waveguide is connected to a side cylindrical section of a capillary portion.

Concerning the arrangement of an optical waveguide 13 (for example, an optical fiber 131) relative to a capillary portion 14, it may be contrived to connect the optical waveguide 13 to a side cylindrical section 144 of the capillary portion 14 as in the embodiment illustrated in FIG. 13 instead of the construction that the optical waveguide 13 is arranged in series with an upper end face 143 of the capillary portion 14. On the inner wall of the side cylindrical section 144, preferably in the inner wall positioned neighborhood of its connected part, a sensitive part (sensitive film) 12 may preferably be formed with a fluorescence- or visible-light-emitting detection substance incorporated therein. This contrivance can facilitate to acquire optical information generated from the sensitive part 12.

Described specifically, a bore T1 is formed through a PFA tube (fluorinated resin tube) T at a position near one end of the PFA tube, and an upper part of the capillary portion 14 is fittedly inserted in the bore T1 and is secured there with an adhesive or the like. The inner diameter and outer diameter of the PFA tube T may be designed, for example, at 0.5 mm and 1.0 mm, respectively. Inside the PFA tube T, an optical waveguide 13, for example, an optical fiber 131 (diameter: 0.25 mm, for example) is arranged. The optical fiber 131 is arranged such that its one end is maintained in contact with an outer cylindrical wall of the side cylindrical section 144 of the capillary portion 14 (see FIG. 13) and the transmission of light can be performed via the optical fiber 131.

Described in detail, the optical fiber 131 delivers measuring light P1 (for example, exciting fluorescent light) to the sensitive part (sensitive film) 12 formed as a film on an inner wall 145 of the capillary portion 14, and also transmits light P2 such as fluorescence or emission produced from the fluorescence source, which exists in the sensitive part 12, to an unillustrated optical measurement unit.

Sign "F" in FIG. 13 designates an optical connecting member, in other words, a ferrule, and sign "18" indicates a holder for holding the ferrule F in place. The PFA tube T and holder 18 are fixed to each other with an adhesive or the like. Sign "146" indicates a tapered section formed as a tip part of the capillary portion 14 (a tapered section the diameter of which gradually increases in a direction toward the upper end face 143).

If some contrivance is made with respect to the configurational correlation between the capillary portion 14 and the optical waveguide 13 depicted in FIG. 13, it is possible to avoid a situation that the optical waveguide 13 connected to the capillary portion 14 would block the capillary portion 14 to interfere with the capillary action under which gingival crevicular fluid is drawn up and also another situation that the end face of the optical waveguide 13 would be smeared (as opposed to the linear arrangement or configuration). The configurational correlation illustrated in FIG. 13 has merits in that the distance between the capillary portion 14 and the optical waveguide 13 can be controlled constant and the formation of the below-described "toothbrush-type" embodiment (see FIG. 15) can be facilitated.

No particular limitation is imposed on the manner of formation of the sensitive part 12 on the inner wall of the capillary portion 14 in the modified embodiment illustrated in FIG. 13. For example, the sensitive part 12 can be arranged on the inner wall of the capillary portion 14 in such a manner as in the above-described eleventh embodiment.

As shown in FIG. 13, it is also preferred to provide the capillary portion 14 with a single or plural bores 14B at a position or positions spaced a predetermined distance or predetermined distances from the tip of the capillary portion 14. As will be described later in Example 20, in the case of a capillary portion provided with no bore, a solution containing detection substances is introduced from the tip to the upper end of the capillary portion. Where the capillary portion 14 is provided with a bore, on the other hand, the introduction of the solution containing the detection substances stops around the bore when the solution is introduced from the tip of the capillary portion 14.

As a consequence, one or more sensitive parts (sensitive films) 12 can be easily formed on the inner wall of the capillary portion 14 at a desired position or desired positions. Further, the detection substances for detecting the substance in the body can be changed at every sensitive part 12 as desired. In other words, different combinations of detection substances can be separately and suitably immobilized on the inner wall at desired positions, respectively. It is, therefore, possible to reduce inhibition, competition or the like between the detection substances themselves although such inhibition, competition or the like would occur if they were incorporated together in the same sensitive part 12.

In addition, the bore or bores 14B each also function as an air vent upon collecting gingival crevicular fluid under capillary action.

When it is desired to arrange a single bore 14B as shown in FIG. 13, the bore 14B may preferably be arranged between a tip 14A of the capillary portion 14 and an upper end 14C of the capillary portion 14 at a position approximately from a half to three quarters the way up from the tip 14A.

When it is desired to arranged plural bores 14B, on the other hand, no particular limitations are imposed on their positions. The plural bores 14B may be arranged at intervals in the longitudinal direction or circumferential direction of the capillary portion 14. These plural bores 14B make it possible to efficiently and surely immobilize a sensitive film.

The arrangement of the plural bores 14B makes it possible to form plural sensitive parts 12 on the inner wall of the capillary portion 14, and also at desired positions. When two bores 14B are arranged at an interval in the longitudinal direction of the capillary portion 14, for example, a sensitive part (sensitive film) 12 can be formed on the inner wall of the capillary portion 14 at a position between its tip 14A and the lower bore 14B, and another sensitive part (sensitive film) 12 can be formed with a different combination of detection substances incorporated therein on the inner wall of the capillary portion 14 at a position between the lower bore 14B and the upper bore (not shown) located above the lower bore 14B toward the upper end 14C of the capillary portion 14. Where a series of multi-step enzyme reactions or plural enzymes are used or even where an enzyme having a potential problem of inhibiting another enzyme reaction (for example, a protein-degrading enzyme such as protease) is used, the arrangement of the plural sensitive parts 12 makes it possible to adequately detect and/or measure a target substance in the body.

Each bore 14B can be formed in the capillary portion 14 by a known bore-forming technology. Upon formation of each bore 14B, the bore size (diameter) of the bore 14B may desirably be set either equal to or smaller than the size of the capillary portion 14, especially the outer diameter of its tip. The bore size of each bore 14B may preferably be from 0.01 to 0.2 mm, with from 0.05 to 0.1 mm being more preferred.

As a method for forming the sensitive part 12 on the inner wall of the capillary portion 14 having the bore 14B, the sensitive part 12 may be formed as in the above-described tenth embodiment or eleventh embodiment. The use of this bore 14B makes it possible to easily form plural sensitive parts 12.

When there is only one bore, for example, a sensitive part 12 can be formed specifically in the following manner. The tip 14A of the capillary portion 14 is sealed, and from the upper end 14C of the capillary portion 14, said upper end 14C being on the side opposite to the tip 14A and having been unsealed, the above-described solution containing the detection substances is introduced under capillary action from the upper end 14C to near the bore 14B within the capillary portion 14. Subsequently, the solution is dried to form the sensitive part 12, with the detection substances being immobilized therein, directly on the inner wall of the capillary portion 14 between the upper end 14C and the bore 14B.

When there are two bores, on the other hand, the solution containing the detection substances is introduced from the upper end 14C to near the proximal bore 14B within the capillary portion 14 as mentioned above. Subsequently, the solution is dried to form a sensitive part 12 with the detection substances immobilized therein. The capillary portion 14 is then held upside down, another solution containing a combination of detection substances (including, for example, an enzyme) different from the above-introduced detection substances is introduced onto the inner wall of the capillary portion 14 between from its tip 14A to the proximal bore 14B. Subsequently, the solution is dried to form a sensitive part 12 with the different detection substances immobilized therein. In this manner, it is possible to form two sensitive parts 12 which are different from each other. It is to be noted that the timing of immobilization into each sensitive part may be changed as desired. For example, after the solutions with their corresponding detection substances contained therein are introduced into the capillary portion 14 from its tip and upper end, respectively, the solutions may be immobilized at the same time.

As in the above-described tenth embodiment, it is preferred to incorporate, in each solution containing its corresponding detection substances, a solution of a diazide compound and an immobilizing agent which, in combination, permit immobilization upon exposure to light (ultraviolet ray).

As described above, the bore or bores 14B can be readily formed by a conventional technology, and moreover, the use of the bore or bores 14B can easily form one or more sensitive parts 12 of high functionality at a desired position or desired positions.

2. System 10 for Detecting a Substance in the Body

Figure 14:
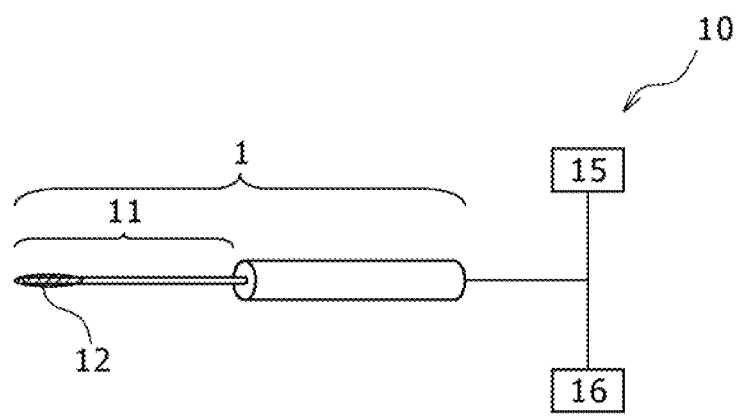
FIG. 14 is a schematic conceptual diagram of a first embodiment of the system for detecting a substance in the body according to the present application.

With reference to FIG. 14, the first embodiment of the system 10 for detecting a substance in the body according to the present application will be described hereinafter. The system 10 for detecting a substance in the body according to the present application is a system for detecting a substance in the body in gingival crevicular fluid, and roughly dividing, is provided with at least a probe 1 for detecting a substance in the body, a light irradiator 15 and a photodetector 16. The system 10 for detecting a substance in the body can also be provided with a dichroic element 17, a collective lens 18 and an optical filter 19 as needed. Each of these elements will hereinafter be described in detail. It is to be noted that the probe 1 for detecting a substance in the body is similar to the above-described probe for detecting a substance in the body according to the present application, and therefore, its description is omitted herein.

(1) Light Irradiator 15

The light irradiator 15 is arranged to irradiate light (for example, exciting fluorescence) onto a sensitive part 12 arranged in the probe 1 for detecting a substance in the body.

No particular limitation is imposed on the kind of light to be irradiated from the light irradiator 15. To have fluorescence or scattering light surely generated from the inside of the sensitive part 12, light which is constant in direction, wavelength and intensity is desired. Examples can be lasers, LEDs, mercury vapor lamps and the like. When a laser is used, no particular limitation is imposed on its kind. Argon ion (Ar) lasers, helium-neon (He—Ne) lasers, dye lasers, Krypton (Kr) lasers and the like can be used either singly or in combination as desired.

(2) Photodetector 16

The photodetector 16 is arranged to detect optical information produced from the inside of the sensitive part 12 upon irradiation of light by the light irradiator 15.

Insofar as the optical information can be detected, no particular limitation is imposed on the type of a photodetector 16 for use in the system 10 for detecting a substance in the body according to the present application, and a known photodetector can be chosen and adopted as desired. For example, fluorophotometers, scattered light meters, transmitted light meters, reflected light meters, diffracted light meters, ultraviolet spectrophotometers, infrared spectrophotometers, Raman spectrophotometers, FRET meters, FISH meters, various other spectrum meters, so-called multichannel photodetectors each including plural photodetectors arranged in arrays, and the like can be adopted either singly or in combination as desired.

(3) Dichroic Element 17

Figure 15:
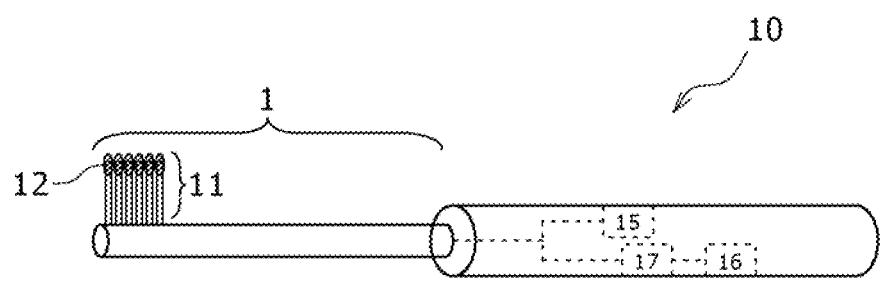
FIG. 15 is a schematic conceptual diagram of a second embodiment of the system for detecting a substance in the body according to the present application.

The system 10 for detecting a substance in the body according to the present application can be provided with a dichroic element 17 (see FIG. 15). The arrangement of this dichroic element 17 makes it possible to select and output necessary optical information only.

No particular limitation is imposed on a dichroic element 17 for use in the system 10 for detecting a substance in the body according to the present application, and depending on the purpose, a known dichroic element can be chosen and used as desired. For example, a dichroic mirror, branching filter or the like can be used.

(4) Collective Lens

Although not shown in any figure, the system 10 for detecting a substance in the body according to the present application can be provided, between the light irradiator 15 and the sensitive part 12, with an exciting collective lens to condense excitation light from the light irradiator 15 onto the sensitive part 12. This collective lens is not essential for the system 10 for detecting a substance in the body according to the present application, but the arrangement of the exciting collective lens makes it possible to perform accurate irradiation of excitation light onto the sensitive part 12.

Although not shown in any figure, the system 10 for detecting a substance in the body according to the present application can be provided, between the sensitive part 12 and the photodetector 16, with a light-receiving collective lens to condense optical information produced from the inside of the sensitive part 12 onto the photodetector 16. This light-receiving collective lens is not essential for the system 10 for detecting a substance in the body according to the present application, but the arrangement of the light-receiving collective lens 18 makes it possible to further intensify signals of optical information such as fluorescence. As a consequence, it is possible to make an improvement in SN ratio.

(5) Optical Filter

Although not shown in any figure, the system 10 for detecting a substance in the body according to the present application can be provided, between the light irradiator 15 and the sensitive part 12, with an exciting optical filter. This exciting optical filter is not essential for the system 10 for detecting a substance in the body according to the present application, but the arrangement of the exciting optical filter makes it possible to selectively irradiate light of desired wavelength onto the sensitive part 12.

Although not shown in any figure, the system 10 for detecting a substance in the body according to the present application can be provided, between the sensitive part 12 and the photodetector 16, with a light-receiving optical filter. This light-receiving optical filter is not essential for the system 10 for detecting a substance in the body according to the present application, but the arrangement of the light-receiving optical filter makes it possible to selectively receive light of desired wavelength from optical information such as fluorescence produced from the inside of the sensitive part 12.

The above-described system 10 for detecting a substance in the body according to the present application can be formed in a "toothbrush type," for example, as illustrated as the second embodiment in FIG. 15. Described more specifically, miniaturization of the whole system can be realized by arranging, inside a handle section, a photodetector 15 such as an excitation LED, a photodetector 16 such as a light-receiving photodiode, and a dichroic element 17 such as a branching filter for extracting optical information such as fluorescence. By configuring the system 10 for detecting a substance in the body into a hand-holdable form as described above, a substance in the body in gingival crevicular fluid can be detected and/or measured in real time and with time everywhere and anywhere without discrimination.

Example 1

Preparation of a sensitive part usable in a probe for detecting a substance in the body according to the present application was actually carried out. As examples of substances to be incorporated in the sensitive part, glucose oxidase, peroxidase and 10-acetyl-3,7-dihydroxyphenoxazine (ADHP) were used in this example. The sensitive part of this example adopted the form that the detection substances were immobilized in a sensitive film. The preparation procedure of the sensitive part in this example was as will be described hereinafter.

1. 10 mM ADHP dissolved in dimethyl sulfoxide (DMSO) was prepared.

2. 10 U/mL horseradish peroxidase (POD) dissolved in purified water was prepared.

3. An aliquot (100 µL) of the 10 mM ADHP prepared in step 1 and an aliquot (200 µL) of the 10 U/mL POD prepared in step 2 were provided, respectively, and after being mixed together, the resulting mixture was diluted with purified water (4.7 mL).

4. 10 U/mL glucose oxidase (GOD) dissolved in purified water was prepared.

5. Aliquots (50 µL each) of the ADHL-POD solution prepared in step 3, 10 U/mL GOD prepared in step 4 and a UV-curable resin ("BIOSURFINE AWP," trade name, product of Toyo Gosei Co., Ltd.) were provided and mixed.

6. An aliquot (20 µL) of the mixture prepared in step 5 was dropped onto a slide glass.

7. The slide glass obtained in step 6 was transferred into a constant temperature chamber, and was then dried at 60° C. for ten minutes.

8. The slide glass dried in step 7 was exposed to UV light for five minutes to cure the UV-curable resin, whereby a sensitive part was prepared on the slide glass.

Figure 16:
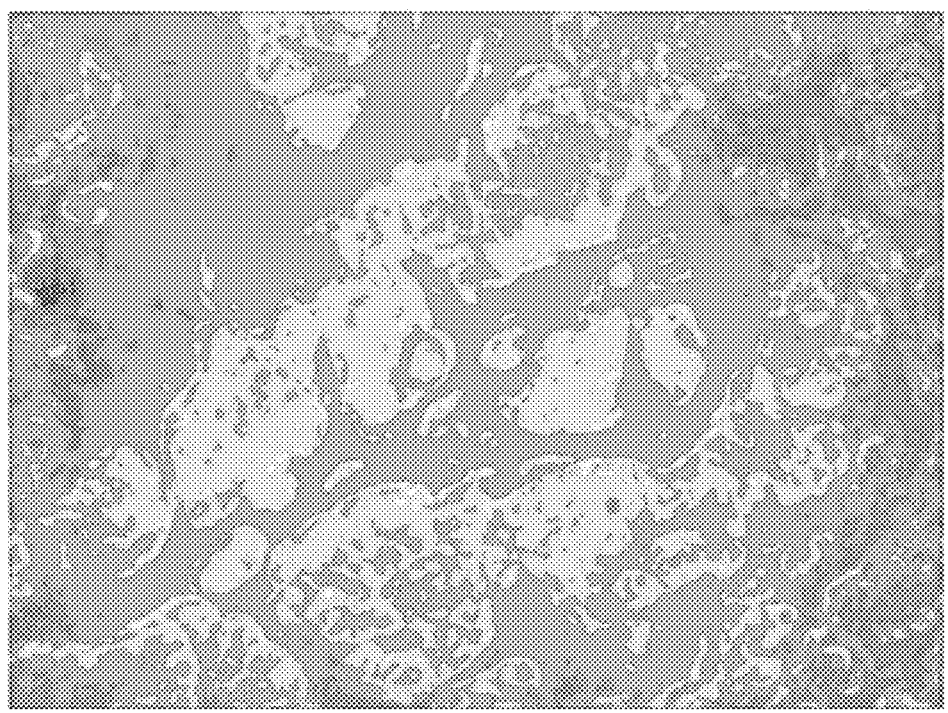
FIG. 16 is an 8× magnification photo of a sensitive part on a slide glass as prepared in Example 1.

An 8× magnification photo of the above-prepared sensitive part is shown in FIG. 16.

As shown in FIG. 16, it was confirmed that the sensitive part was porous and hence good in substance permeability.

Example 2

In this example, the sensitive part prepared in Example 1 was tested for physical strength. The following experimental procedure was followed.

1. The slide glass prepared in Example 1 and carrying the sensitive part formed thereon was provided.

2. The slide glass was observed at a surface thereof under a stereomicroscope.

3. A periodontal probe ("PDT Sensor Probe Type U.S.," trade name, product of Williame) was provided.

4. The sensitive part on the slide glass was rubbed at a surface thereof to apply a load of 20 g while observing the surface under the stereomicroscope.

5. The surface of the sensitive part was observed for any separation by naked eye and under the stereomicroscope.

As a result of the observation, the surface of the sensitive part on the slide glass was found to include no separation and was proven to exhibit sufficient strength even when used in a probe for detecting a substance in the body.

Example 3

This example was conducted to confirm that optical measurement would be feasible at the sensitive part on the slide glass prepared in Example 1.

For the optical measurement of the reactive part, the following fluorometric system was used. Specifically, the following two types of systems were used for the fluorometric measurement of resorufin produced from ADHP.

Employed as one of the systems were an optical-fiber-coupled excitation light source ("LE-1xxx," trade name, product of WT&T Inc.), a spectroscope ("MCPD-7700," trade name, product of Otsuka Electronics Co., Ltd.), a box with a built-in excitation light filter, a box with a built-in fluorescence filter, and an optical fiber-probe combination composed of an excitation light optical fiber and fluorescence optical fiber bundled together and a collective lens arranged at a tip. The light source, the box with the built-in excitation light filter, the spectroscope and the box with the built-in fluorescence filter were connected together by optical fibers, the box with the built-in excitation light filter was connected to the excitation light optical fiber in the optical fiber-probe combination, and the box with the built-in fluorescence filter was connected to the fluorescence optical fiber in the optical fiber-probe combination. As the other system, "FLE-1000" (trade name, product of Nippon Sheet Glass Co., Ltd.) was employed. This system is internally provided with an excitation LED, a light-receiving photodiode and a branching filter for extracting fluorescence, and by using the optical fiber-probe combination to which the system is fitted, can irradiate excitation light onto a target of measurement and can detect the resulting fluorescence.

1. A D-glucose solution was prepared by the following procedure.

(1) Phosphate buffered saline (PBS) was prepared with purified water.

(2) 4 g/L D-glucose solution was prepared.

(3) Using the phosphate buffered saline prepared in step (1) and the 4 g/L D-glucose solution prepared in step (2), a D-glucose solution of desired concentration was prepared.

2. Next, the optical fiber-probe combination of the above-described fluorometric system was arranged on the sensitive part on the slide glass prepared in Example 1.

3. Fluorescence intensity was measured by the fluorometric system with or without dropping the reaction solution, which had been prepared in step 1, onto the sensitive part.

Figure 17:
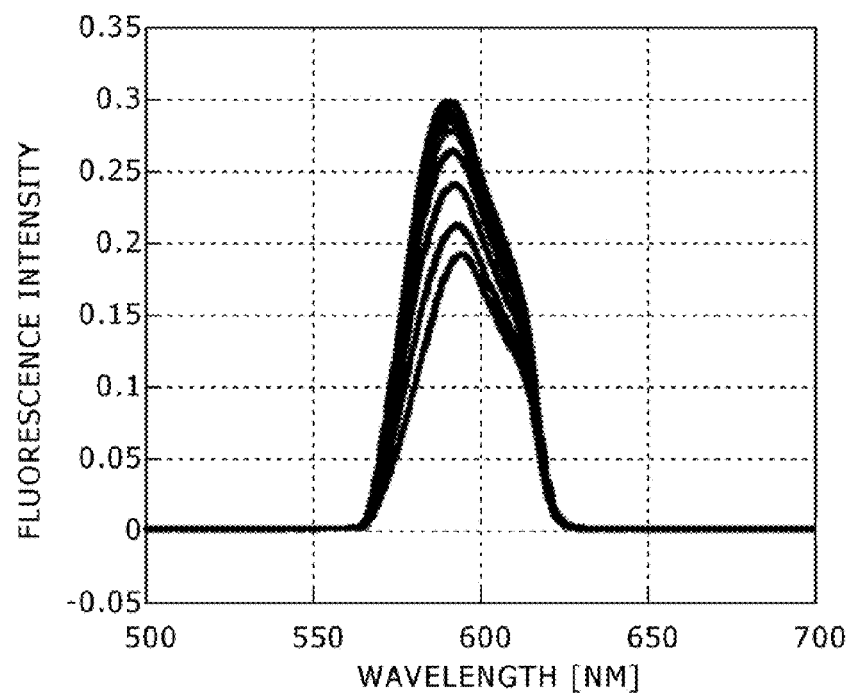
FIG. 17 is a graph of fluorescence intensity as measured by dropping 10 μL of a 100 mg/dL D-glucose/PBS solution onto the sensitive part in Example 3.
Figure 18:
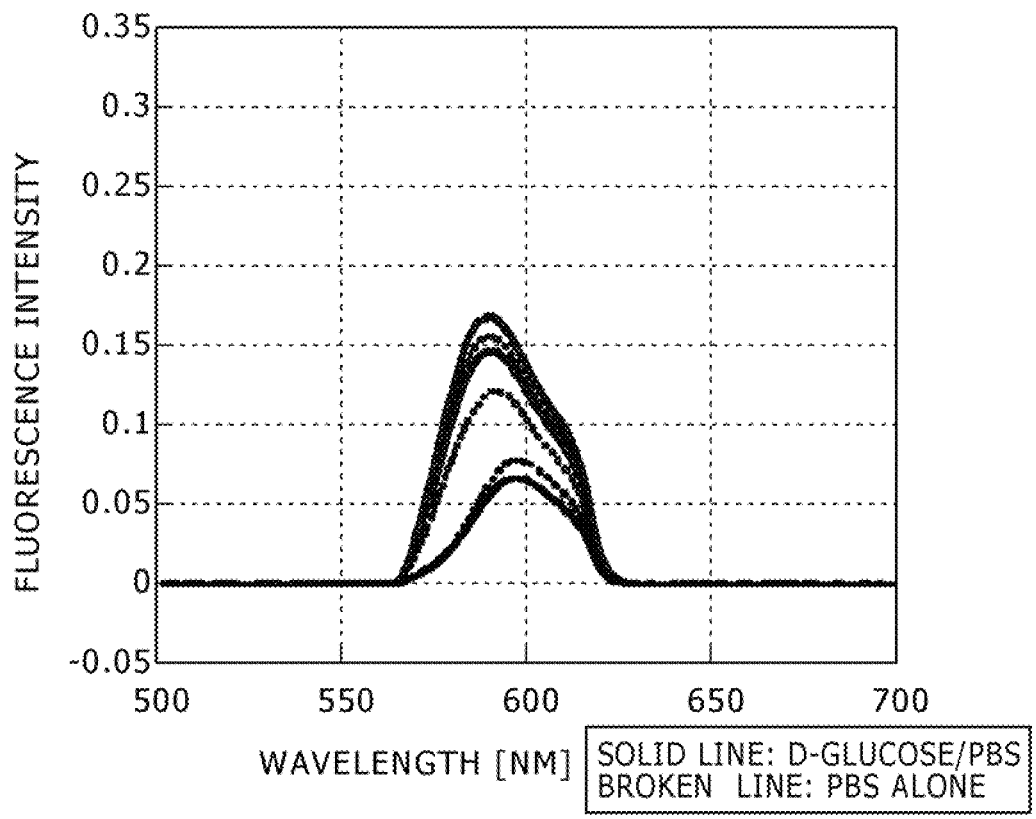
FIG. 18 is a graph showing differences in fluorescence intensity between when 10 μL of phosphate buffered saline (PBS) alone were dropped and when 10 μL of the 100 mg/dL D-glucose/PBS solution were dropped, both onto the sensitive part in Example 3.

The measurement results are shown in FIG. 17 and FIG. 18. FIG. 17 is a graph of fluorescence intensities as measured by dropping 10 μL of a 100 mg/dL D-glucose/PBS solution onto the sensitive part. The graph of FIG. 17 shows, in ascending order, fluorescence intensities at the 0th second, 60th second, 120th second, 180th second, 240th second, 300th second, 360th second, 420th second, 480th second and 540th second after the dropping.

As shown in FIG. 17, it was possible to confirm that by the dropping of the D-glucose solution onto the sensitive part, fluorescence from the inside of the sensitive part was measured.

FIG. 18 a graph showing differences in fluorescence intensity between when 10 μL of the phosphate buffered saline (PBS) alone were dropped and when 10 μL of the 100 mg/dL D-glucose/PBS solution were dropped, both onto the sensitive part. In FIG. 18, the solid curves (D-glucose solution) and the dotted curves (PBS alone) indicate, in ascending order, fluorescence intensities at the time of dropping, two minutes later and five minutes later.

As shown in FIG. 18, it was found that, when the D-glucose solution was dropped, the fluorescence intensity was clearly higher two minutes later and five minutes later compared with that of control group in which PBS alone was dropped.

Example 4

A probe for detecting a substance in the body according to the present application was actually produced in this example. As examples of substances to be incorporated in a sensitive part of the probe for detecting a substance in the body according to the present application, glucose oxidase, peroxidase and 10-acetyl-3,7-dihydroxyphenoxazine (ADHP) were used in this example.

1. 10 mM ADHP dissolved in dimethyl sulfoxide (DMSO) was prepared.

2. 10 U/mL horseradish peroxidase (POD) dissolved in purified water was prepared.

3. An aliquot (100 μL) of the 10 mM ADHP prepared in step 1 and an aliquot (200 μL) of the 10 U/mL POD prepared in step 2 were provided, respectively, and after being mixed together, the resulting mixture was diluted with purified water (4.7 mL).

4. 10 U/mL glucose oxidase (GOD) dissolved in purified water was prepared.

5. Aliquots (50 μL each) of the ADHP-POD solution prepared in step 3, 10 U/mL GOD prepared in step 4 and a UV-curable resin ("BIOSURFINE AWP," trade name, product of Toyo Gosei Co., Ltd.) were provided and mixed.

6. A plastic-made or glass-made, optical fiber (outer diameter: 0.25 mm) was provided.

7. The optical fiber provided in step 6 was cut into a length of approx. 3 cm, and the length of optical fiber was inserted into a ferrule for an FC connector.

8. Onto a tip of the optical fiber on a side opposite to the ferrule, the mixture prepared in step 5 was dropped.

9. The optical fiber with the mixture dropped thereon was transferred into a constant temperature chamber, and was then dried at 60° C. for ten minutes.

10. The optical fiber was then exposed to UV light for five minutes to cure the UV-curable resin, whereby a probe for detecting a substance in the body according to the present application was actually produced.

Example 5

In this example, fluorescence produced from each of an aqueous solution of resorufin and a sensitive part was measured by using a probe for detecting a substance in the body having no sensitive part. This example was an experiment to determine whether or not an optical fiber would function as an optical waveguide in the probe for detecting a substance in the body according to the present application.

1. Assembly of Fluorometric System (1) An optical fiber provided with an FC connector was connected to "FLE-1000."

(2) An adapter for connecting FC connectors to each other was fitted to the FC connector described in step (1).

(3) The probe for detecting a substance in the body having no sensitive part was fitted in the adapter described in step (2).

2. Preparation of Aqueous Solution of Resorufin (1) Purified water (10 mL) was provided.

(2) In the purified water provided in step (1), resorufin (0.004 g) was mixed to prepare a saturated aqueous solution. In this step, undissolved resorufin precipitated.

(3) When dilution was needed, a supernatant of the saturated aqueous solution prepared in step (2) was provided, followed by the addition of purified water to effect the dilution.

3. Fluorometric Measurement in Aqueous Solution of Resorufin (1) In each of the aqueous solution of resorufin (saturated concentration) prepared in step 2 and its ⅓-fold dilution aqueous solution, a tip of the probe for detecting a substance in the body produced in step 1 and having no sensitive part for the fluorometric system was immersed to conduct measurement of resorufin.

4. Fluorometric Measurement in Sensitive Part (1) Onto the sensitive part (on the slide glass) formed in Example 1, the D-glucose solution prepared in Example 3 was dropped.

(2) The tip of the probe for detecting a substance in the body produced in step 1 and having no sensitive part for the fluorometric measurement system was brought into contact with the sensitive part on the slide glass described in step (1), and fluorometric measurement was performed.

Figure 19:
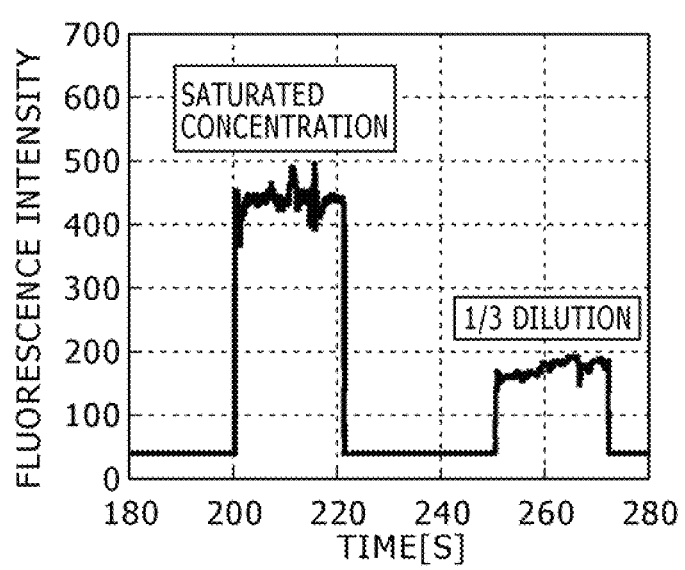
FIG. 19 is a graph showing the results of measurement of fluorescence emitted from an aqueous solution of resorufin in Example 5 as conducted by using a probe for detecting a substance in the body having no sensitive part.
Figure 20:
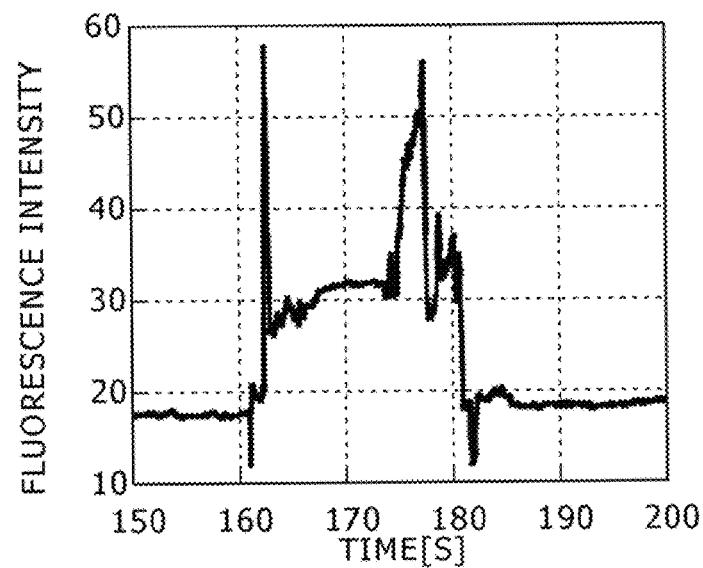
FIG. 20 is a graph showing the results of measurement of fluorescence emitted from a sensitive part on a slide glass in Example 5 as conducted by using the probe for detecting a substance in the body having no sensitive part.

The measurement results are shown in FIG. 19 and FIG. 20. FIG. 19 is a graph showing the results of measurement by the probe for detecting a substance in the body, which had no sensitive part, of fluorescence produced from the inside of the aqueous solution of resorufin. FIG. 20 is a graph showing the results of measurement by the probe for detecting a substance in the body, which had no sensitive part, of fluorescence produced from the inside of the sensitive part on the slide glass.

As shown in FIG. 19 and FIG. 20, it has been confirmed that fluorescence produced from each of the inside of an aqueous solution of resorufin and the inside of a sensitive part on a slide glass can be measured by using a probe for detecting a substance in the body having no sensitive part. From this result, it has also been confirmed that an optical fiber can function as an optical waveguide in the probe for detecting a substance in the body according to the present application.

Example 6

In this example, an experiment was conducted to confirm that D-glucose would be actually detectable by using the probe for detecting a substance in the body according to the present application produced in Example 4.

1. Assembly of Fluorometric System (1) An optical fiber provided with an FC connector was connected to "FLE-1000."

(2) An adapter for connecting FC connectors to each other was fitted to the FC connectors described in step (1).

(3) The probe for detecting a substance in the body produced in Example 4 was fitted in the adapter described in step (2).

2. Detection of D-glucose (1) A plastic-made spectroscopic cell of 1 cm cube was provided.

(2) An aliquot (2 mL) of the D-glucose solution (100 mg/dL (blood sugar level in normal subjects)) prepared in Example 3 was injected into the cell provided in step (1).

(3) The probe for detecting a substance in the body in the fluorometric system assembled in step 1 was immersed in the D-glucose solution in the cell, and fluorometric measurement was performed.

Figure 21:
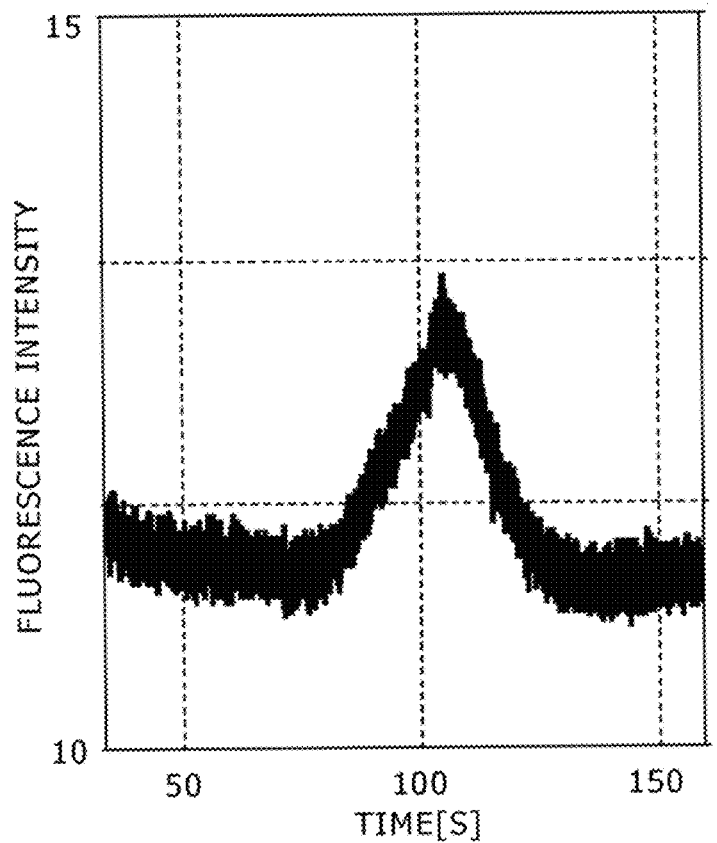
FIG. 21 is a graph showing the results of detection of D-glucose in Example 6 as conducted by using a probe for detecting a substance in the body according to the present application.

The results of the fluorometric measurement are shown in FIG. 21.

FIG. 21 is a graph showing the results of detection of D-glucose as performed by using the probe for detecting a substance in the body according to the present application. As shown in FIG. 21, it has been found that, when the probe for detecting a substance in the body according to the present application is used, the individual enzymes and dye immobilized in the sensitive part of the probe for detecting a substance in the body induce a series of reactions to form resorufin and the measurement of the intensity of fluorescence from the resorufin makes it possible to detect D-glucose.

Example 7

A probe for detecting a substance in the body according to the present application, which was provided with a capillary portion, was actually produced in this example. As examples of substances to be incorporated in a sensitive part of the probe for detecting a substance in the body, glucose oxidase, peroxidase and 10-acetyl-3,7-dihydroxyphenoxazine (ADHP) were used in this example.

1. Example 7-1

Formation of a Sensitive Part in the Form of a Sensitive Film Between a Capillary Portion and an Optical Fiber (1) 10 mM ADHP dissolved in dimethyl sulfoxide (DMSO) was prepared.

(2) 10 U/mL horseradish peroxidase (POD) dissolved in purified water was prepared.

(3) An aliquot (100 µL) of the 10 mM ADHP prepared in step (1) and an aliquot (200 µL) of the 10 U/mL POD prepared in step (2) were provided, respectively, and after being mixed together, the resulting mixture was diluted with purified water (4.7 mL).

(4) 10 U/mL glucose oxidase (GOD) dissolved in purified water was prepared.

(5) Aliquots (50 µL each) of the ADHP-POD solution prepared in step (3), 10 U/mL GOD prepared in step (4) and a UV-curable resin ("BIOSURFINE AWP," trade name, product of Toyo Gosei Co., Ltd.) were provided and mixed.

(6) A plastic-made or glass-made, optical fiber (outer diameter: 0.25 mm) was provided.

(7) The optical fiber provided in step (6) was cut into a length of approx. 3 cm, and the length of optical fiber was inserted into a ferrule for an FC connector.

(8) On a tip of the optical fiber on a side opposite to the ferrule, the mixture prepared in step (5) was coated, and further, a capillary portion was fitted.

(9) The optical fiber with the capillary portion fitted thereon was transferred into a constant temperature chamber, and was then dried at 60° C. for ten minutes.

(10) The optical fiber was then exposed to UV light for five minutes to cure the UV-curable resin, whereby the capillary portion was adhered to the optical fiber and a sensitive part was formed in the form of a sensitive film between the capillary portion and the optical fiber.

2. Example 7-2

Formation of a Sensitive Part in the Form of a Sensitive Film on an Inner Wall of a Capillary Portion (1) 10 mM ADHP dissolved in dimethyl sulfoxide (DMSO) was prepared.

(2) 10 U/mL horseradish peroxidase (POD) dissolved in purified water was prepared.

(3) An aliquot (100 µL) of the 10 mM ADHP prepared in step (1) and an aliquot (200 µL) of the 10 U/mL POD prepared in step (2) were provided, respectively, and after being mixed together, the resulting mixture was diluted with purified water (4.7 mL).

(4) 10 U/mL glucose oxidase (GOD) dissolved in purified water was prepared.

(5) Aliquots (50 µL each) of the ADHP-POD solution prepared in step (3), 10 U/mL GOD prepared in step (4) and a UV-curable resin ("BIOSURFINE AWP," trade name, product of Toyo Gosei Co., Ltd.) were provided and mixed.

(6) A plastic-made or glass-made, optical fiber (outer diameter: 0.25 mm) was provided.

(7) The optical fiber provided in step (6) was cut into a length of approx. 3 cm, and the length of optical fiber was inserted into a ferrule for an FC connector.

(8) On a tip of the optical fiber on a side opposite to the ferrule, a capillary portion was fitted.

(9) The mixture prepared in step (5) was drawn up into the capillary portion. The capillary portion with the mixture introduced therein was transferred into a constant temperature chamber, and was then dried at 60° C. for ten minutes.

(10) The capillary portion was then exposed to UV light for five minutes to cure the UV-curable resin, whereby a sensitive part was formed in the form of a sensitive film in the capillary portion.

3. Example 7-3

Formation of a Sensitive Part in the Form of a Sensitive Film by Immobilizing Detection Substances Directly on an Inner Wall of a Capillary Portion (1) 10 mM ADHP dissolved in dimethyl sulfoxide (DMSO) was prepared.

(2) 10 U/mL horseradish peroxidase (POD) dissolved in purified water was prepared.

(3) An aliquot (100 μL) of the 10 mM ADHP prepared in step (1) and an aliquot (200 μL) of the 10 U/mL POD prepared in step (2) were provided, respectively, and after being mixed together, the resulting mixture was diluted with purified water (4.7 mL).

(4) 10 U/mL glucose oxidase (GOD) dissolved in purified water was prepared.

(5) Aliquots (50 μL each) of the ADHP-POD solution prepared in step (3) and 10 U/mL GOD prepared in step (4) were provided and mixed.

(6) A plastic-made or glass-made, optical fiber (outer diameter: 0.25 mm) was provided.

(7) The optical fiber provided in step (6) was cut into a length of approx. 3 cm, and the length of optical fiber was inserted into a ferrule for an FC connector.

(8) On a tip of the optical fiber on a side opposite to the ferrule, a capillary portion was fitted.

(9) The mixture prepared in step (5) was drawn up into the capillary portion. The capillary portion with the mixture introduced therein was transferred into a constant temperature chamber, and was then dried at 60° C. for ten minutes. As a result, the detection substances were immobilized directly on an inner wall of the capillary portion to form a sensitive part.

Example 8

This example was conducted to confirm that the probes each for detecting a substance in the body of Example 7-1 and Example 7-3 produced in Example 7 would be able to detect D-glucose.

1. Assembly of Fluorometric System (1) An optical fiber provided with an FC connector was connected to "FLE-1000."

(2) Adapters for connecting FC connectors to each other were fitted to the FC connectors described in step (1), respectively.

(3) The probes each for detecting a substance in the body of Example 7-1 and Example 7-3 produced in Example 7 were fitted in the adapters described in step (2), respectively.

2. Detection of D-glucose (1) Plastic-made spectroscopic cells of 1 cm cube were provided.

(2) Aliquots (1 mL) of the D-glucose solution prepared in Example 3 were injected into the respective cells provided in step (1). As controls, phosphate buffered saline was injected into the remaining cells.

(3) The probe for detecting a substance in the body in each fluorometric system assembled in step 1 was immersed in the D-glucose solution in the cell or the phosphate buffered saline in the cell, and fluorometric measurement was performed. Further, a probe for detecting a substance in the body having no sensitive part was additionally provided, and its response to the phosphate buffered saline was also tested (see "bare" in FIG. 22).

Figure 22:
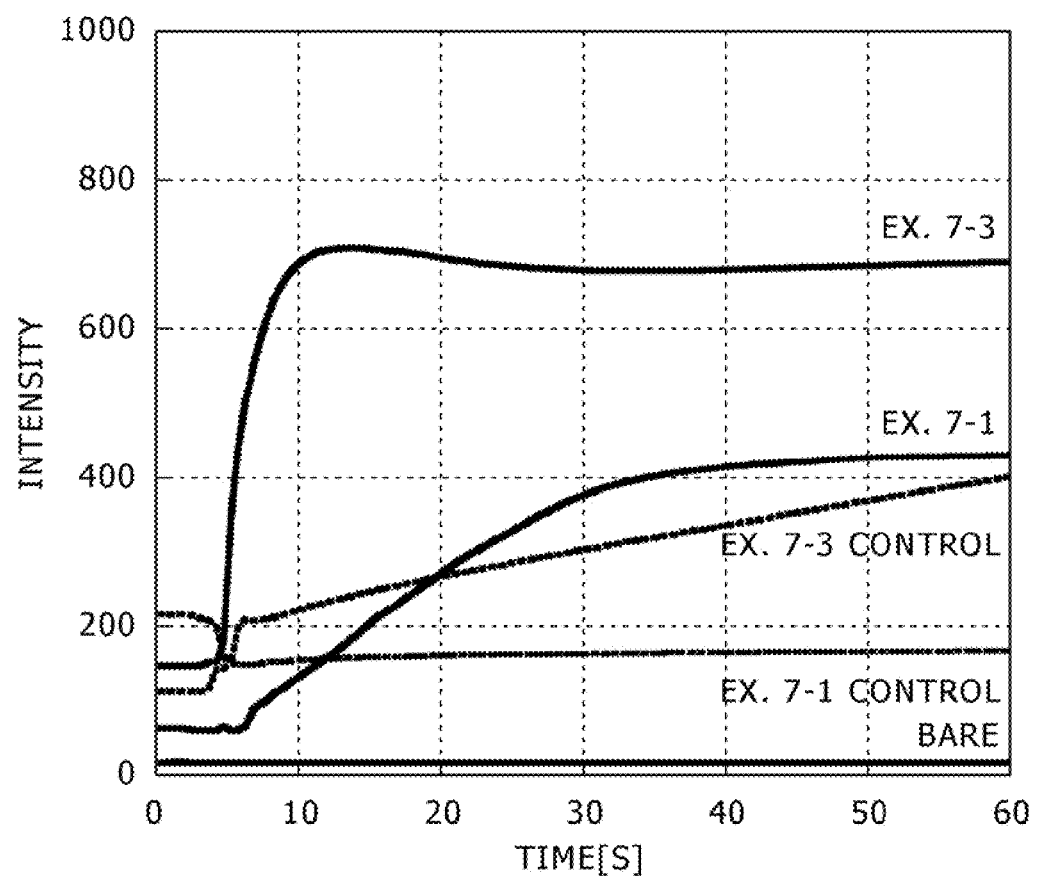
FIG. 22 is a graph showing differences in fluorescence intensity between when probes each for detecting a substance in the body according to the present application were immersed in aliquots (1 mL) of phosphate buffered saline (PBS) alone and when they were immersed in aliquots (1 mL) of a solution of D-glucose, both in Example 8.

The results of the fluorometric measurement are shown in FIG. 22. FIG. 22 is a graph showing differences in fluorescence intensity between when the probes each for detecting a substance in the body according to the present application were immersed in aliquots (1 mL) of phosphate buffered saline (PBS) alone, respectively, and when they were immersed in aliquots (1 mL) of the solution of D-glucose, respectively. As shown in FIG. 22, it was found that the fluorescence intensities (solid curves) obtained when the probes were immersed in the solution of D-glucose were clearly higher than those of the controls (dotted curves) obtained when the probes were immersed in PBS alone.

Example 9

This example was conducted to confirm that the quantification of D-glucose would be feasible by using the probe for detecting a substance in the body of Example 7-3 produced in Example 7.

1. Assembly of Fluorometric System (1) An optical fiber provided with an FC connector was connected to "FLE-1000."

(2) An adapter for connecting FC connectors to each other was fitted to the FC connector described in step (1).

(3) The probe for detecting a substance in the body of Example 7-3 produced in Example 7 was fitted in the adapter described in step (2).

2. Detection of D-glucose (1) Plastic-made spectroscopic cells of 1 cm cube were provided.

(2) Aliquots (1 mL each) of D-glucose solutions adjusted to 0 g/L, 0.5 g/L and 1 g/L in a similar manner as in Example 3 were injected into the respective cells provided in step (1).

(3) The probe for detecting a substance in the body in the fluorometric system assembled in step 1 was immersed in the D-glucose solutions in the cells to perform fluorometric measurement.

Figure 23:
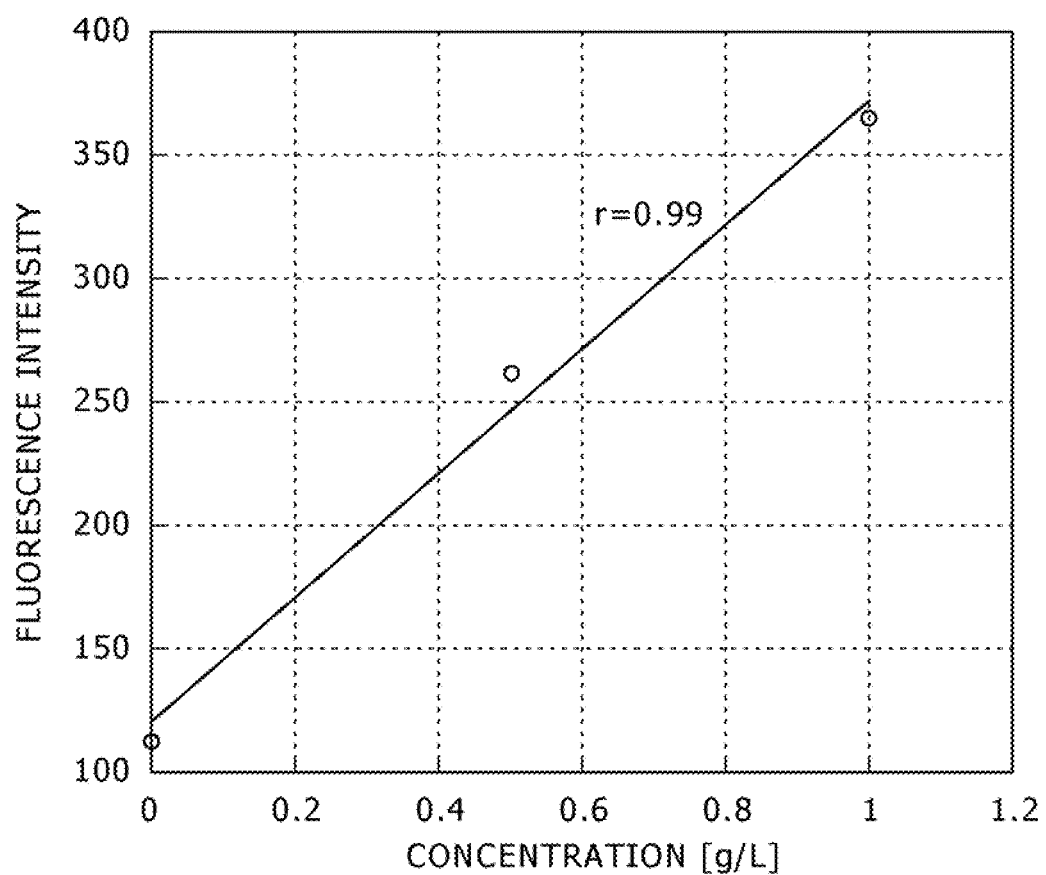
FIG. 23 is a graph showing the results of quantification of D-glucose in Example 9 as conducted by using a probe for detecting a substance in the body according to the present application.

The results of the fluorometric measurement are shown in FIG. 23. As shown in FIG. 23, it was found that the fluorescence intensity increased in proportion to the concentration of the D-glucose solution. From this result, it has been proven that the use of a probe for detecting a substance in the body according to the present application can perform not only the detection of a substance in the body but also even the quantification of the substance in the body.

Example 10

An experiment was conducted on the formation of a sensitive part making use of a diazide compound as an illustrative photoreactive compound. Employed as detection substances were glucose oxidase (GOD), peroxidase (POD), and 10-acetyl-3,7-dihydroxyphenoxazine (ADHP). GOD (product of Sigma-Aldrich Corporation), POD (product of Sigma-Aldrich Corporation), ADHP (product of AnaSpec Inc.), and a photoimmobilizing solution containing the diazide compound and a high molecular resin, gel or compound (product of Girasol Bio Inc.) were provided, and an aqueous solution (hereinafter called "the photoimmobilizing aqueous solution A") was prepared. As an optical waveguide, a plastic-made optical fiber (diameter: 0.25 mm, length: 2 cm) was provided. One end of the optical fiber was fitted in a ferrule for an FC connector. A tip of the optical fiber on an opposite end was immersed for ten seconds or so in the sensitive-part-forming, photoimmobilizing aqueous solution A, and was then pulled out of the photoimmobilizing aqueous solution A. After being dried for more than 30 minutes at room temperature, the optical fiber was exposed to ultraviolet ray to form a sensitive part, which contained GOD, POD and ADHP, on an end face opposite to the FC connector. Subsequently, an optical-fiber-type fluorophotometer with a built-in excitation light source (product of Nippon Sheet Glass Co., Ltd.) was provided. The ferrule for the FC connector, in which the optical fiber with the sensitive part arranged thereon was fitted, was optically connected to an optical fiber portion of the fluorophotometer. A 1 g/L solution of D-glucose in phosphate buffered solution (PBS) was prepared as a sample solution. The end face of the optical fiber, on which the sensitive part is arranged, was immersed in the sample solution, and the resulting fluorescence was measured.

Figure 24:
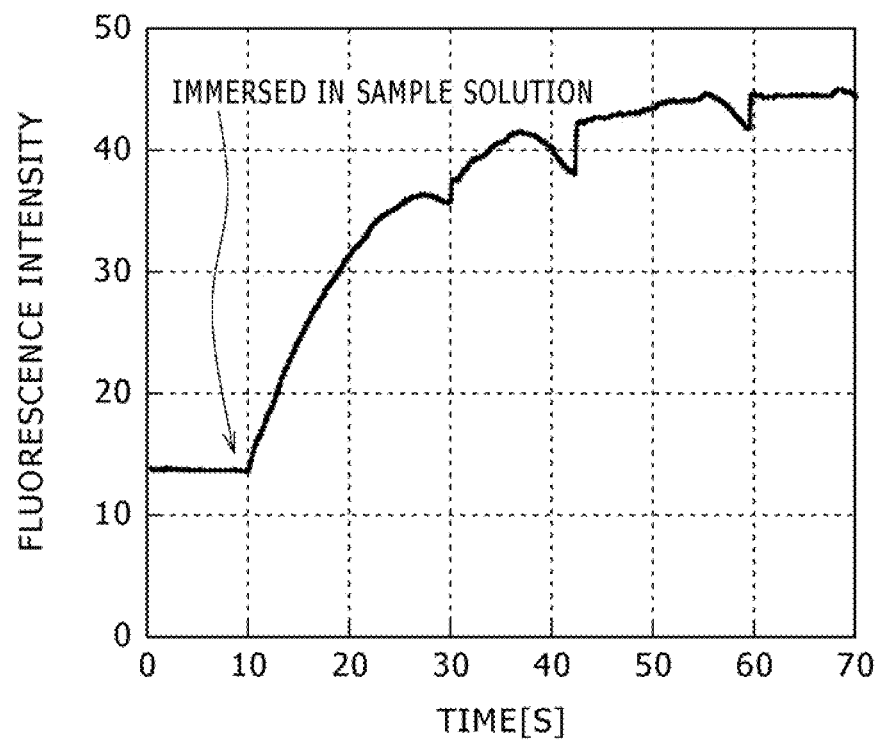
FIG. 24 is a graph showing the results of fluorescence measurement in Example 10 by a probe for detecting a substance in the body of a construction that a sensitive part was formed on an end face of an optical fiber by using an aqueous photoimmobilizing solution with a photoreactive diazide compound contained therein.

The measurement results are shown in FIG. 24. As appreciated from the graph shown in FIG. 24, it was possible to measure fluorescence from shortly after the immersion of the sensitive part of the optical fiber in the sample part, and the results were good.

Example 11

Using the same photoimmobilizing aqueous solution A as that employed in Example 10, an experiment was next conducted to perform the immobilization of the detection substances on the inner wall of a capillary portion making up a probe for detecting a substance in the body. Firstly, a plastic-made capillary portion of 0.4 mm in outer diameter and 2 cm in length was provided. An aliquot (0.2 µL) of the same photoimmobilizing aqueous solution A as that employed in Example 10 was provided, and was drawn up into the capillary portion. The capillary portion contained the photoimmobilizing aqueous solution A attracted therein. It was possible to visually confirm the progress of the attraction of the solution. After being dried for more than 30 minutes at room temperature, the capillary portion was exposed to ultraviolet ray to form a sensitive part on the inner wall of the capillary portion. Different from water-soluble, UV-curable resins which have heretofore been employed commonly, smooth attraction of the solution into the capillary portion under capillary force was confirmed firstly. Subsequently, the same sample solution as that employed in Example 10 was provided, and the capillary portion was held in place on a slide glass by a double-stick tape and was observed under a fluorescence microscope. Onto a tip of the capillary portion, an aliquot (5 µL) of the sample solution was dropped, and the sample solution was attracted into the capillary portion. The capillary portion was excited by green light, and fluorescent image was visually observed. The sample solution was attracted inside the capillary portion. It was possible to observe fluorescence from the inside of the capillary portion. It was also possible to confirm that despite the formation of the sensitive part on the inner wall of the capillary portion, the capillary force was not lost at all, no blocking took place either, and the sample solution was smoothly loaded.

It is to be noted that, in similar comparative experiments conducted with known water-soluble, UV-curable resins, blocking took place in most of the experiments and the loading was difficult. To conduct a detailed fluorescent observation, the capillary portion was cut into a length of approx. 2 mm, and its response to the sample solution was fluorescently observed likewise.

Figure 25A:
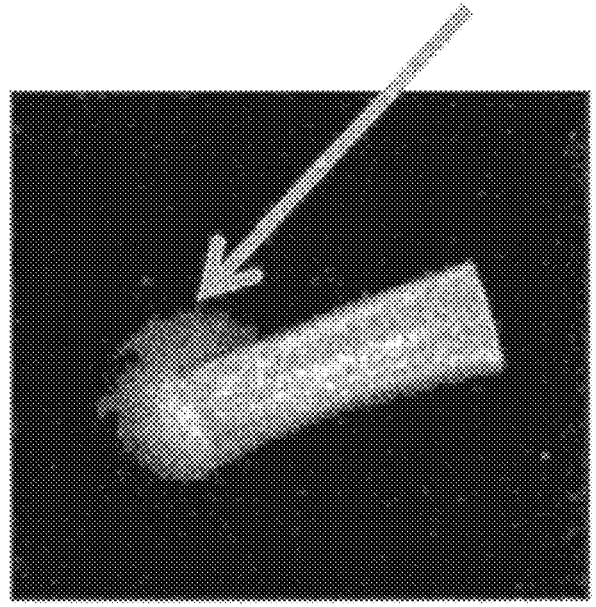
FIGS. 25A and 25B are fluorescent observation images in Example 11. Specifically.
Figure 25B:
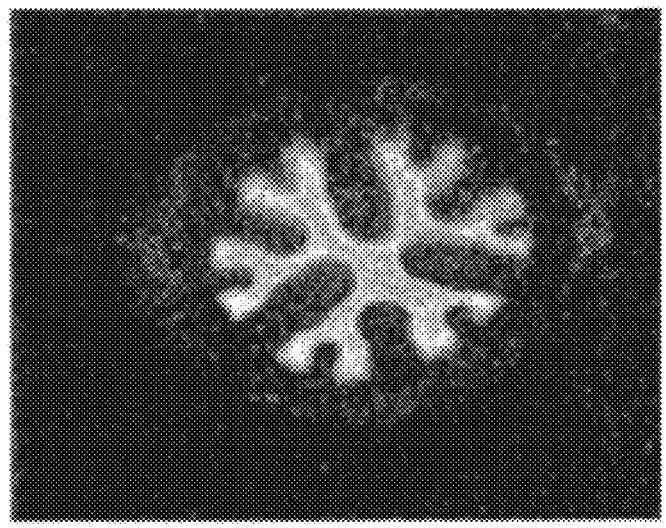

Fluorescent observation images are shown in FIGS. 25A and 25B. Based on the image taken from the side (see the image of FIG. 25A), it was possible to confirm that fluorescence was produced from the entirety of the capillary portion. In other words, it was possible to confirm that the reactions took place in the entirety of the sensitive part formed on the inner wall of the capillary portion. Based on the image of a cross-section (see the image of FIG. 25B), it was possible to confirm that fluorescence was produced from the inside of the capillary portion.

It has been confirmed from these observation results that a sample solution can be smoothly drawn up to the side of an inner wall of a capillary portion, said inner wall being provided with a sensitive part formed thereon, intended enzyme reactions and the like are allowed to proceed in the sensitive part immobilized on the inner wall, and therefore, fluorescence can be produced.

Example 12

A plastic-made optical fiber (diameter: 0.25 mm, length: 2 cm) fitted in a ferrule for an FC connector was next fitted in a PFA tube (inner diameter: 0.5 mm), and the PFA tube and the ferrule were adhered to each other. The capillary portion of Example 11 was fitted in the PFA tube such that an end face of the capillary portion came to contact with an end face of the optical fiber. The PFA tube and capillary portion were then adhered to each other to produce a probe.

Figure 26:
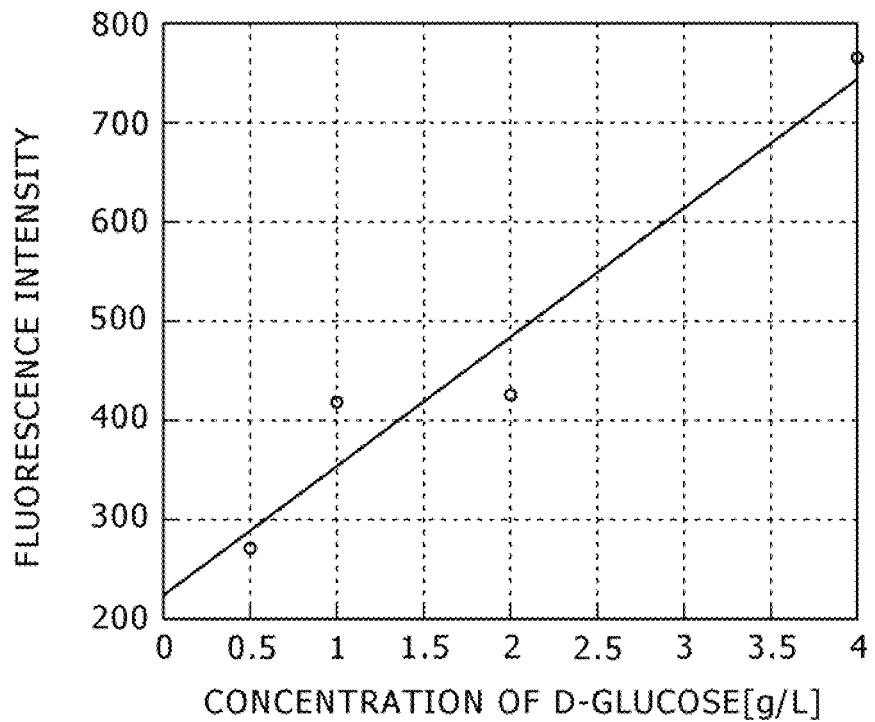
FIG. 26 is a graph showing the results of fluorescence measurement in Example 12. Specifically.

The fluorophotometer employed in Example 10 and the probe were optically connected together as in Example 10. As sample solutions, 0, 0.5, 1, 2 and 4 g/L solutions of D-glucose in PBS were prepared. The tip of the capillary portion of the probe was immersed for two seconds in the sample solutions to perform fluorometric measurement. The measurement results of fluorescence intensity at the respective D-glucose concentrations upon elapsed time of 20 seconds are shown in FIG. 26. As shown in the graph of FIG. 26, it has been confirmed that fluorescence can be measured from a sample solution attracted in a capillary portion.

Example 13

In this example, an experiment was conducted on an alcohol (ethanol) detection system. As detection substances, alcohol oxidase, peroxidase and 10-acetyl-3,7-dihydroxyphenoxazine (ADHP) were used. Firstly, a sensitive part was formed in the following manner. Alcohol oxidase (product of Sigma-Aldrich Corporation), peroxidase (POD, product of Sigma-Aldrich Corporation) and 10-acetyl-3,7-dihydroxyphenoxazine (ADHP, product of AnaSpec Inc.) were provided, and a 9 U/mL aqueous solution of the alcohol oxidase, a 1.5 U/mL aqueous solution of peroxidase and a 50 µg/mL solution of ADHP in dimethyl sulfoxide (DMSO) were prepared. An aliquot (1.3 µL) of the aqueous alcohol-oxidase solution, an aliquot (1.5 µL) of the aqueous peroxidase solution and an aliquot (2.5 µL) of the ADHP solution, all of which had been prepared above, were mixed together, and then, purified water (310 µL) was added to dilute the resulting mixture. The photoimmobilizing solution with the diazide compound contained therein (product of Hirasol Bio Inc.) was added and mixed with the thus-diluted mixture such that the diazide compound amounted to 0.0625 w/v %. As a consequence, an "aqueous photoimmobilizing solution B" was prepared. A capillary portion of 0.4 mm in outer diameter and 2 cm in length was next provided, and an aliquot (0.2 µL) of the aqueous photoimmobilizing solution B was drawn up into the capillary portion. After being dried, the capillary portion was exposed to ultraviolet ray to immobilize the detection substances. As a result, a sensitive part with the enzymes and substrate incorporated therein was formed (immobilized) on an inner wall of the capillary portion.

A solution of ethanol in phosphate buffered saline (PBS) was next provided as a sample solution. Its ethanol concentration was set at 0.03 w/v %. If this concentration is detected in blood, it is considered to be a human drunkenness concentration. On a stage of a fluorescence microscope, the capillary portion with the sensitive part formed thereon was held in place. An aliquot (5 µL) of the sample solution was dropped onto the tip of the capillary portion, and was attracted into the capillary portion.

As a result, fluorescence was observed corresponding to a flow of the sample solution through the capillary portion, and therefore, the sensitive part formed on the inner wall of the capillary portion was confirmed to function as intended.

Subsequently, the production of a probe for detecting a substance in the body similar to the embodiment of FIG. 13 was conducted by the procedure to be described hereinafter. A plastic-made optical fiber of 0.25 mm in diameter and 2 cm in length was provided, and was fitted in an FC-type ferrule. A PFA tube of 2 cm in length and 0.5 mm in inner diameter was provided, and around a middle part of the PFA tube, a transverse bore was formed. The PFA tube was fitted on a side cylindrical section of the capillary portion such that the PFA tube and the side cylindrical section intersect at right angles. The PFA tube was fitted on the optical fiber to bring the optical fiber into contact with the side cylindrical section of the capillary portion. The ferrule and PFA tube were adhered together, and the PFA tube and capillary portion were adhered together. As a consequence, the transmission of excitation light via the optical fiber in the ferrule results in the entrance of the excitation light into the side cylindrical section of the capillary portion, thereby exciting resorufin in the sensitive part formed on the inner wall of the light-transmitting capillary portion. It is, therefore, possible to realize a construction that can perform fluorometric measurement by receiving through the optical fiber fluorescence produced from the resorufin.

A fluorophotometer of the optical fiber system (manufactured by Nippon Sheet Glass Co., Ltd.) was next provided. Via an FC-type adapter, the above-described detection probe provided in this example was fitted to the fluorophotometer. Further, the ethanol-containing sample solution provided in this example was kept warm at 37° C., and an aliquot (5 μL) of the sample solution was provided in a weighing dish. After the detection probe was immersed for five seconds in the sample solution, the probe was pulled out of the sample solution, and fluorometric measurement was performed. As a control, a PBS solution was provided, and similar fluorometric measurement was performed.

Figure 27:
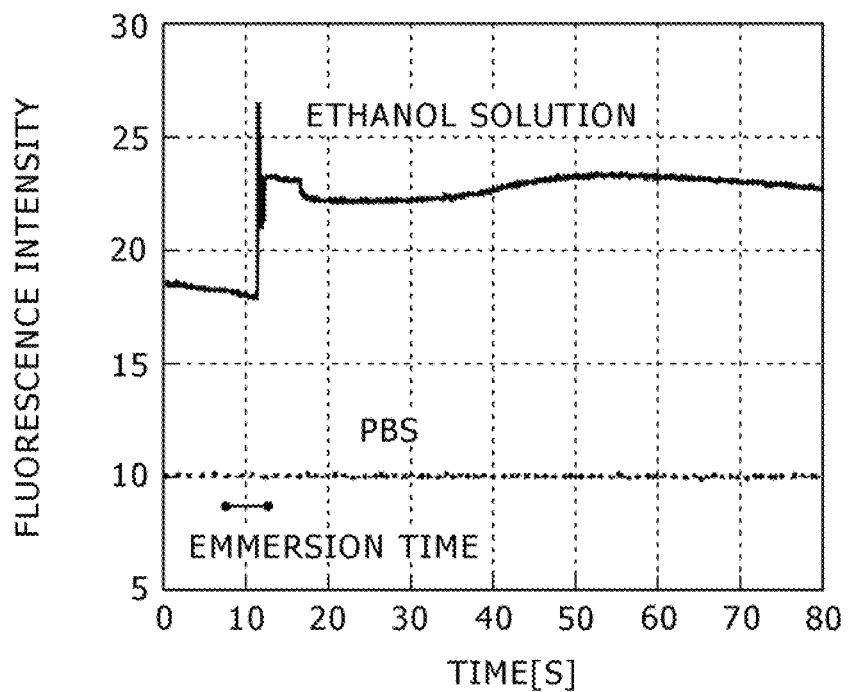
FIG. 27 is a graph showing the results of fluorescence measurement in Example 13. Specifically.

As a result of the fluorometric measurement, a pronounced increase in fluorescence was observed with the ethanol-containing sample solution, but no increase was observed with PBS. FIG. 27 is a graph showing the results of the fluorometric measurement in this example. From the results shown in this graph, it has been confirmed that the detection of ethanol is feasible by a detection probe of a construction that a sensitive part is arranged on the inner wall of a capillary portion and an optical fiber, which functions as a light waveguide, is connected to a side cylindrical section of the capillary portion.

As an enzyme reaction accelerates with the concentration of a substrate, the concentration of the substrate can be estimated from the concentration of a final product. It is, therefore, possible to find the concentration of ethanol based on the intensity of fluorescence.

Further, gingival crevicular fluid is known to be similar to the plasma component of blood. By measuring gingival crevicular fluid, the concentration of ethanol in blood can be quantified accordingly. The probe for detecting a substance in the body and system according to the present application can, therefore, provide a technology that can measure the concentration of alcohol in blood noninvasively rather than invasively.

Example 14

The detection of D-glucose is feasible by changing the detection substances for the sensitive part to glucose oxidase (GOD), peroxidase (POD) and 10-acetyl-3,7-dihydroxyphenoxazine (ADHP) in the detection probe of the construction adopted in Example 13.

Figure 28:
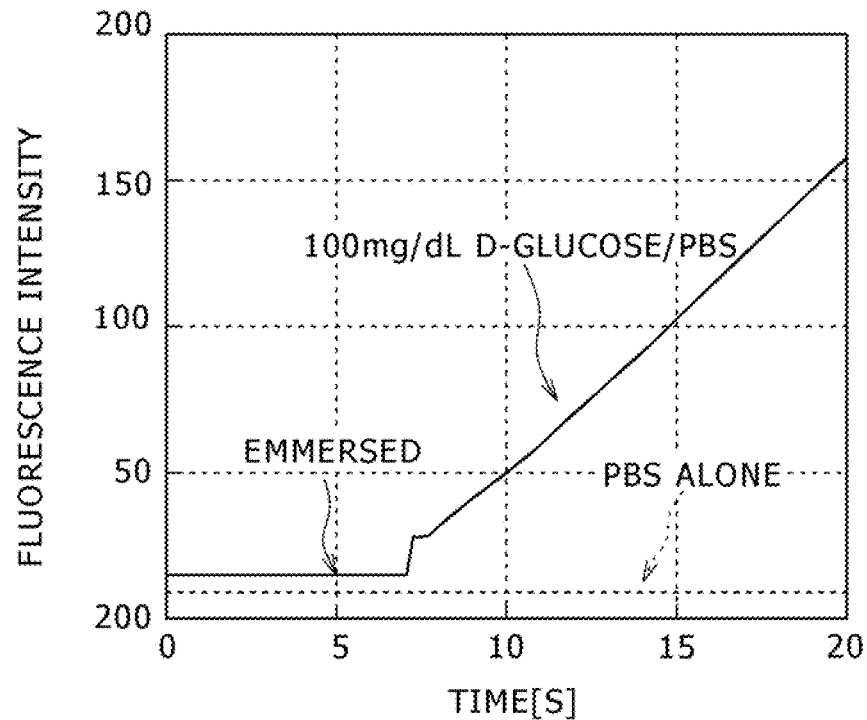
FIG. 28 is a graph showing the results of fluorescence measurement in Example 14. Specifically.

FIG. 28 is a graph showing the results of fluorometric measurement for the detection of D-glucose, which made use of the detection probe of the construction adopted in Example 13. As appreciated from this graph, fluorescence was clearly measured from the PBS containing D-glucose at 100 mg/dL concentration as opposed to PBS as a control.

Example 15

In this example, an experiment was conducted on a uric acid detection system.

Firstly, a sensitive part for the detection of uric acid was formed. Uricase (product of Sigma-Aldrich Corporation), peroxidase (POD, product of Sigma-Aldrich Corporation) and 10-acetyl-3,7-dihydroxyphenoxazine (ADHP, product of AnaSpec Inc.) were provided, and a 9 U/mL aqueous solution of uricase, a 1.5 U/mL aqueous solution of peroxidase and a 50 μg/mL solution of ADHP in dimethyl sulfoxide (DMSO) were prepared. An aliquot (1.3 μL) of the aqueous uricase solution, an aliquot (1.5 μL) of the aqueous peroxidase solution and an aliquot (2.5 μL) of the ADHP solution, all of which had been prepared above, were mixed together, and then, purified water (310 μL) was added to dilute the resulting mixture. The photoimmobilizing solution with the diazide compound contained therein (product of Hirasol Bio Inc.) was added and mixed with the thus-diluted mixture such that the diazide compound amounted to 0.0625 w/v %. As a result, an "aqueous photoimmobilizing solution C" was prepared for the formation of a sensitive part.

A capillary portion of 0.4 mm in outer diameter and 2 cm in length was next provided, and an aliquot (0.2 μL) of the aqueous photoimmobilizing solution C was drawn up into the capillary portion under capillary action. After being dried, the capillary portion was exposed to ultraviolet ray to form (immobilize) a sensitive part.

A solution of sodium urate in phosphate buffered saline (PBS) was next provided as a sample solution. Its concentration was set at 0.01 w/v %, because 7 mg/dL (0.007 w/v %) corresponds to the standard value for high uric acid level and 0.01 w/v % in blood is a concentration suspicious of a high uric acid level. On a stage of a fluorescence microscope, the capillary portion capable of functioning as a detection probe was held in place. An aliquot (5 μL) of the sample solution was dropped onto the tip of the capillary portion, and was attracted into the capillary portion. Fluorescence was observed corresponding to a flow of the sample solution through the capillary portion. As a result, the sensitive part formed on the inner wall of the capillary portion was confirmed to function as a uric acid detection system.

Subsequently, a probe for detecting a substance in the body similar to the embodiment of FIG. 13 was produced by a similar procedure as in Example 13 or Example 14. Via an FC-type adapter, the probe was fitted to a fluorophotometer of the optical fiber system (manufactured by Nippon Sheet Glass Co., Ltd.)

The sample solution provided in this example was next kept warm at 37° C., and an aliquot (5 μL) of the sample solution was provided in a weighing dish. After the probe was immersed for five seconds in the sample solution, the probe was pulled out of the sample solution, and fluorometric measurement was performed. As a control, PBS was provided and measured likewise.

Figure 29:
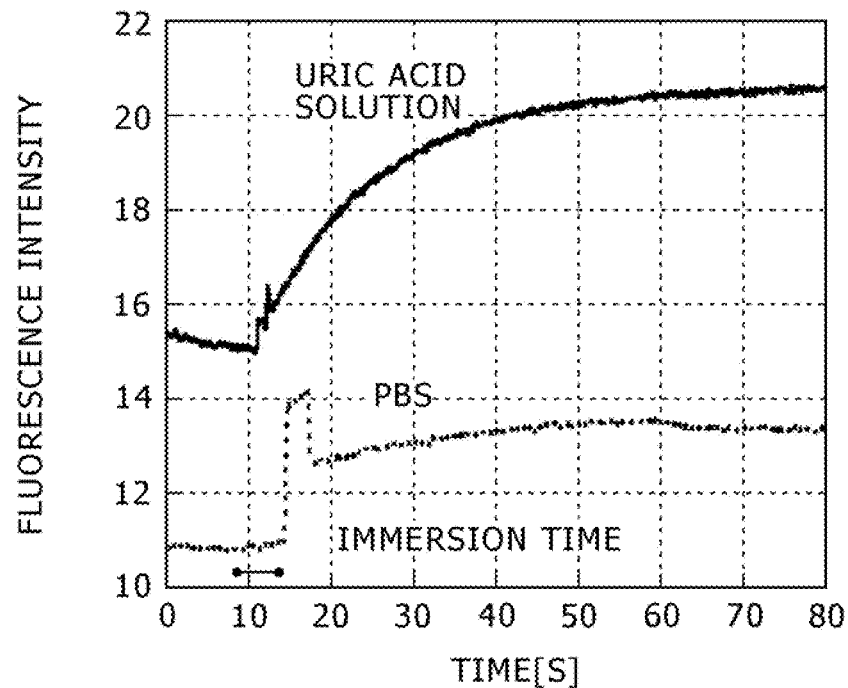
FIG. 29 is a graph showing the results of fluorescence measurement in Example 15. Specifically.

As a result of the measurement, a pronounced increase in fluorescence was observed with the sample solution containing uric acid, but an increase was small with PBS as the control. The graph shown in FIG. 29 indicates that the sample solution with uric acid contained therein (uric acid solution) was measured higher in fluorescence intensity compared with the uric-acid-free PBS as the control.

From the foregoing results, it has been found that the detection of uric acid is actually feasible by a detection probe of a construction that a sensitive part is arranged on the inner wall of a capillary portion and a light waveguide is connected to a side cylindrical section of the capillary portion. As an enzyme reaction accelerates with the concentration of a substrate, the concentration of the substrate can be estimated from the concentration of a final product. It is, therefore, possible to find the concentration of uric acid based on the intensity of fluorescence.

Further, gingival crevicular fluid is known to be similar to the plasma component of blood. By measuring gingival crevicular fluid, the concentration of uric acid in blood can be quantified accordingly. The probe for detecting a substance in the body and system according to the present application is, therefore, effective as a technology that can measure the concentration of uric acid in blood noninvasively rather than invasively.

It is to be noted that the incorporation of a boronic acid compound as a detection substance in the sensitive parts adopted in the above-described examples makes it possible to perform fluorometric detection of sugar contained in gingival crevicular fluid on the basis of the reaction principle represented by the above-described chemical reaction formula (1).

Example 16

In this example, an experiment was conducted on a lactic acid detection system.

Firstly, a sensitive part for the detection of lactic acid was formed. Lactate oxidase (product of Sigma-Aldrich Corporation), peroxidase (POD, product of Sigma-Aldrich Corporation) and 10-acetyl-3,7-dihydroxyphenoxazine (ADHP, product of AnaSpec Inc.) were provided. A 1 U/μL aqueous solution of lactate oxidase, a 1.5 U/mL aqueous solution of peroxidase and a 50 μg/mL solution of ADHP in dimethyl sulfoxide (DMSO) were prepared. An aliquot (10 μL) of the aqueous lactate oxidase solution, an aliquot (15 μL) of the aqueous peroxidase solution and an aliquot (9 μL) of the ADHP solution, all of which had been prepared above, were mixed together, and then, purified water (280 μL) was added to dilute the resulting mixture. The photoimmobilizing solution (product of Hirasol Bio Inc.) was added and mixed with the thus-diluted mixture such that the diazide compound amounted to 0.0625 w/v %. As a result, an "aqueous photoimmobilizing solution D" was prepared for the formation of a sensitive part.

A capillary portion of 0.4 mm in outer diameter and 3 cm in length was next provided, and an aliquot (5 μL) of the aqueous photoimmobilizing solution D was provided. An end of the capillary portion was immersed in the aqueous photoimmobilizing solution D, and the aqueous photoimmobilizing solution D was drawn up into the capillary portion under capillary action. After being dried, the capillary portion was exposed to ultraviolet ray to form (immobilize) a sensitive part. As a result, a sensitive film of the enzymes and substrate was immobilized on the inner wall of the capillary portion.

Subsequently, a probe for detecting a substance in the body of this example was produced in a similar manner to the production manner of the above-described probe for detecting a substance in the body of Example 15 except that the above-described sensitive part for the detection of lactic acid was employed. The probe was optically connected to the optical fiber fitted to a fluorophotometer with a built-in excitation light source and photodetector ("FLE-1000," trade name, manufactured by Nippon Sheet Glass Co., Ltd.). It is, therefore, possible to irradiate excitation light from the side wall of the capillary portion and to measure fluorescence produced from resorufin formed through the enzyme reactions in the capillary portion.

As a sample solution, a solution of lactic acid (L-(+)-lactic acid, product of Sigma-Aldrich Corporation) in phosphate buffered saline (PBS) was provided. Its concentration was set at 2.0 mM. This 2.0 mM is the normal value of blood lactic acid level, and any value higher than this value is suspicious of lactic acidosis. After the tip of the detection probe was immersed for five seconds in an aliquot (5 μL) of the lactic-acid-containing sample solution kept warm at 37° C. in a weighing dish, the probe was pulled out of the sample solution, and fluorometric measurement was performed. As a control, PBS was provided, and fluorometric measurement was performed likewise.

Figure 30:
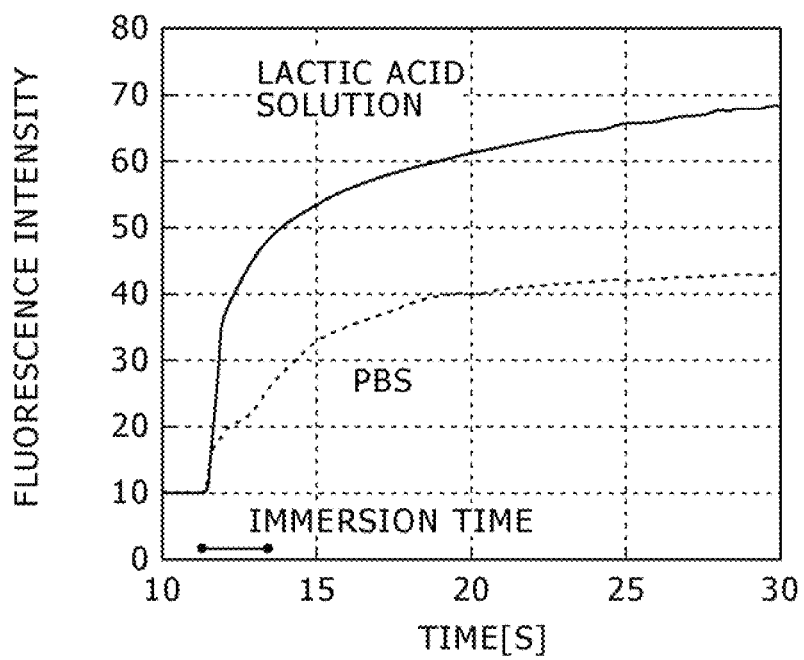
FIG. 30 is a graph showing the results of fluorescence measurement in Example 16. Specifically.

As a result of the fluorometric measurement, a pronounced increase was observed in fluorescence intensity with the lactic-acid-containing sample solution, but an increase was small with PBS (see FIG. 30). From the results, it has been found that the use of a probe with a sensitive film formed on the inner wall of a capillary portion enables the detection of lactic acid.

As an enzyme reaction accelerates with the concentration of a substrate, the concentration of the substrate can be estimated from the concentration of a final product. Measurement was feasible at the normal value, that is, 2.0 mM. At an abnormal value of high concentration greater than the normal value, measurement is hence feasible. It is possible to find the concentration of lactic acid based on the intensity of fluorescence. Further, gingival crevicular fluid is known to be similar to the plasma component of blood. By measuring gingival crevicular fluid, the concentration of lactic acid in blood can be quantified accordingly. The probe for detecting a substance in the body has, therefore, been confirmed to provide a technology that can measure the concentration of lactic acid in blood noninvasively rather than invasively.

Example 17

In this example, an experiment was conducted on a glycated protein detection system.

Firstly, a sensitive part for the detection of a glycated protein was formed. Protease (product of Sigma-Aldrich Corporation), fructosyl-amino acid oxidase (product of Sigma-Aldrich Corporation), peroxidase (POD, product of Sigma-Aldrich Corporation) and 10-acetyl-3,7-dihydroxyphenoxazine (ADHP, product of AnaSpec Inc.) were provided. A 0.7 U/μL aqueous solution of protease, a 0.7 U/μL aqueous solution of fructosyl-amino acid oxidase, a 1.5 U/mL aqueous solution of peroxidase and a 50 μg/mL solution of ADHP in dimethyl sulfoxide (DMSO) were prepared.

An aliquot (10 μL) of the aqueous solution of fructosyl-amino acid oxidase, an aliquot (15 μL) of the aqueous peroxidase solution and an aliquot (9 μL) of the ADHP solution, all of which had been prepared above, were mixed together, and then, purified water (280 μL) was added to dilute the resulting mixture, whereby a protease-free solution was prepared. To the solution, the aqueous protease solution was also added to prepare a mixed solution of all the detection substances. The mixed solution showed white turbidity. It was, therefore, possible to gather that degradation of the non-protease enzymes by protease had taken place.

It was, accordingly, decided to separately prepare a protease-free solution and a solution of protease alone.

The photoimmobilizing solution (product of Hirasol Bio Inc.) was added and mixed with the protease-free solution such that the diazide compound amounted to 0.0625 w/v %. As a result, a protease-free, "aqueous photoimmobilizing solution E1" was prepared for the formation of a sensitive part.

The solution of protease alone was prepared by adding purified water (305 µL) to an aliquot (10 µL) of the aqueous protease solution such that the aqueous protease solution was diluted. The photoimmobilizing solution (product of Hirasol Bio Inc.) was added and mixed with the solution of protease alone such that the diazide compound amounted to 0.0625 w/v %. As a result, a protease-containing, "aqueous photoimmobilizing solution E2" was prepared for the formation of a sensitive part.

A capillary portion of 0.4 mm in outer diameter and 3 cm in length was next provided. From one side of a left half of the capillary portion, an aliquot (0.2 µL) of the protease-containing, aqueous photoimmobilizing solution E2 was drawn up under capillary action. From a right half of the capillary portion on the side opposite to the left half, an aliquot (0.2 µL) of the protease-free, aqueous photoimmobilizing solution E1 was drawn up under capillary action. After being dried, the capillary portion was exposed to ultraviolet ray. As a result, two kinds of sensitive parts were formed (immobilized) on the inner wall of the capillary portion, specifically a sensitive film of the protease on the side of the left half of the capillary portion, and a sensitive film of the enzymes other than the protease (fructosyl-amino acid oxidase and peroxidase) and the substrate (ADHP) on the side of the right half of the capillary portion.

Subsequently, a probe for detecting a substance in the body of this example was produced in a similar manner as the production manner of the above-described probe for detecting a substance in the body of Example 15 except that the above-described sensitive part for the detection of the glycated protein was employed. Upon optical connection of the probe to the optical fiber fitted to a fluorophotometer with a built-in excitation light source and photodetector ("FLE-1000," trade name, manufactured by Nippon Sheet Glass Co., Ltd.), the optical fiber was inserted into the probe from the side of the sensitive film of the enzymes other than the protease (fructosyl-amino acid oxidase and peroxidase) and the substrate (ADHP). The inserted end was used as an inner end, and the opposite end on the side of the sensitive film of protease was used as an outer end. As a consequence, the optical fiber inserted in the ferrule comes into contact with the side wall of the capillary portion at a part thereof where the sensitive film of the enzymes other than the protease (the fructosyl-amino acid oxidase and peroxidase) and the substrate (ADHP) is immobilized on the inner side.

Solutions of glycated albumin (product of Sigma-Aldrich Corporation) and albumin (product of Sigma-Aldrich Corporation) in phosphate buffered saline (PBS) were provided. Their concentrations were set at 5 g/dL. As described above, this 5 g/dL is the normal value of albumin in serum. Both of the solutions were mixed together such that the glycated albumin amounted to 20 w/v % of the total albumin content (the sum of the glycated albumin and albumin). The resultant mixture was provided as a sample solution. As described above, this value of 20 w/v % is a value exceeding the normal value a little. If it is possible to measure such a value, the value can be used for the diagnosis of a blood sugar level.

The sample solution kept warm at 37° C., and an aliquot (5 µL) of the sample solution was provided in a weighing dish heated at 37° C. After the outer end of the detection probe was immersed for five seconds in the sample solution, the detection probe was pulled out of the sample solution, and fluorescence was measured. As controls, a 5 g/dL solution of albumin in PBS and PBS were provided, and fluorometric measurement was performed likewise.

Figure 31:
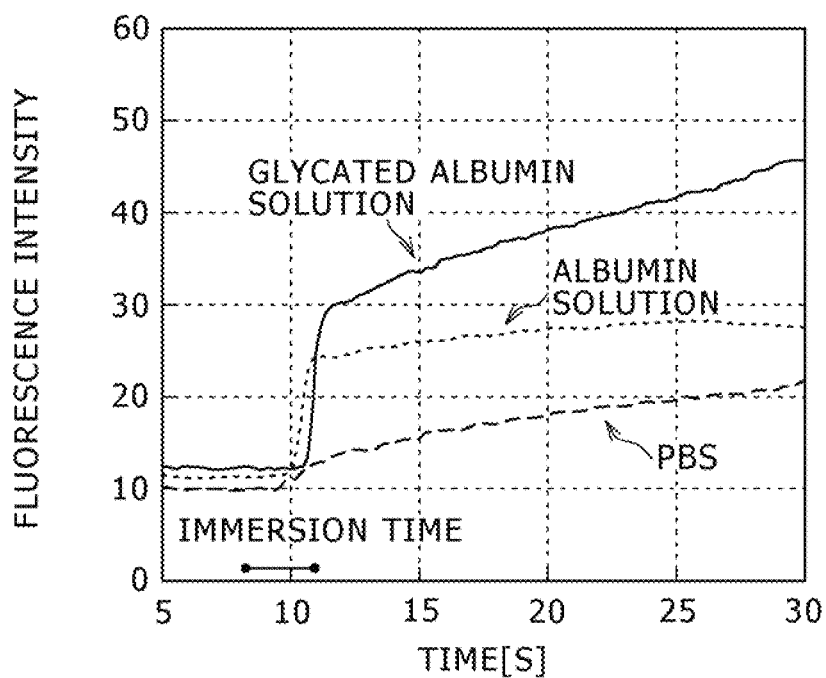
FIG. 31 is a graph showing the results of fluorescence measurement in Example 17. Specifically.

As a result of the fluorometric measurement, the results with the sample solution containing the glycated albumin, the sample solution of albumin alone and PBS are shown in FIG. 31. From a comparison between albumin and PBS, an increase in fluorescence intensity by albumin was large, and fluorescence owing to the existence of albumin was observed. It has been confirmed that with the sample solution containing glycated albumin, an increase in fluorescence intensity is large compared with the sample solution of albumin, the effect of albumin itself is ignorable, and the detection of glycated albumin is feasible.

As the enzyme reaction accelerates with the concentration of the glycated albumin as a substrate, the concentration of the substrate can be estimated from the concentration of a final product. Measurement was feasible at a concentration exceeding the normal value a little, so that at an abnormal value of a concentration higher than the above-mentioned concentration, measurement is feasible. It is possible to find the concentration of the glycated albumin based on the intensity of fluorescence. Further, gingival crevicular fluid is known to be similar to the plasma component of blood. By measuring gingival crevicular fluid, the concentration of the glycated albumin in blood can be quantified accordingly. It is, therefore, understood that the probe for detecting a substance in the body and system according to the present application can provide a technology that can measure the concentration of glycated albumin in blood noninvasively rather than invasively.

Depending on the kind of a protein-degrading enzyme, the substrate specificity differs. When protease of low substrate specificity is used as in this example, the glycated proteins in serum are all degraded so that the resulting probe can be used for the measurement of fructosamine. When a protein-degrading enzyme having high specificity to glycated albumin is used, the measurement of glycated albumin alone is feasible. A protein-degrading enzyme having high specificity to glycated albumin is known, and is used in "LUCICA GA" (trade name, product of Asahi Kasei Pharma Corporation), a commercially-available test agent. By using such protein-degrading enzymes having different substrate specificity, it is possible to measure specific glycated proteins such as not only fructosamine but also glycated albumin and glycated hemoglobin.

Example 18

In this example, an experiment was conducted on a creatine detection system and a creatinine detection system.

Firstly, sensitive parts were formed for the detection of creatinine and creatine, respectively. It is to be noted that creatinine is converted to creatine under the action of creatininase.

Creatininase (product of Sigma-Aldrich Corporation), creatinase (product of Sigma-Aldrich Corporation), sarcosine oxidase (product of Sigma-Aldrich Corporation), peroxidase (POD, product of Sigma-Aldrich Corporation) and 10-acetyl-3,7-dihydroxyphenoxazine (ADHP, product of AnaSpec Inc.) were provided. A 1 U/µL aqueous solution of creatininase, a 1 U/µL aqueous solution of creatinase, a 0.5 U/µL aqueous solution of sarcosine oxidase, a 1.5 U/mL aqueous solution of peroxidase and a 50 μg/mL solution of ADHP in dimethyl sulfoxide (DMSO) were prepared.

Based on the above-prepared solutions, a creatininase-containing aqueous solution and a creatininase-free aqueous solution were prepared.

The creatininase-containing aqueous solution was prepared by mixing an aliquot (10 μL) of the aqueous creatininase solution, an aliquot (10 μL) of the aqueous creatinase solution, an aliquot (10 μL) of the aqueous sarcosine-oxidase solution, an aliquot (15 μL) of the aqueous peroxidase solution and an aliquot (9 μL) of the ADHP solution and then adding purified water (260 μL) to the resulting mixture to dilute the same. On the other hand, the creatininase-free aqueous solution was prepared by using the respective enzymes and substrate at similar concentrations except for the addition of purified water (10 μL) in place of the aqueous creatininase solution. The photoimmobilizing solution (product of Girasol Bio Inc.) was added and mixed with each of the aqueous solutions to be 0.0625 w/v %. As a result, a creatininase-containing, "aqueous photoimmobilizing solution F" and a creatininase-free, "aqueous photoimmobilizing solution FN" were prepared for the formation of sensitive parts.

Subsequently, two capillary portions of 0.4 mm in outer diameter and 3 cm in length were provided. Aliquots (0.2 μL) of the individual immobilizing solutions, that is, the aqueous photoimmobilizing solution F and aqueous photoimmobilizing solution FN were drawn up into the respective capillary portions. After being dried, the capillary portions were exposed to ultraviolet ray. As a result, a sensitive film of all the enzymes and the substrate and another sensitive film of the enzymes other than creatininase and the substrate were immobilized on the inner walls of the capillary portions, respectively, whereby sensitive parts were formed. In this manner, a detection probe having a creatininase-containing sensitive film and a detection probe having a creatininase-free sensitive film were produced.

Two probes each for detecting a substance in the body of this example were next produced in a similar manner as the production manner of the above-described probe for detecting a substance in the body of Example 15 except that the above-described sensitive parts for the detection of creatine and the like were employed. The probes were each optically connected an optical fiber fitted to a fluorophotometer with a built-in excitation light source and photodetector ("FLE-1000," trade name, manufactured by Nippon Sheet Glass Co., Ltd.). It is, therefore, possible to irradiate excitation light from the side wall of each capillary portion and to measure fluorescence produced from resorufin formed through the enzyme reactions in the capillary portion.

Two kinds of solutions, specifically an aqueous solution of creatinine (product of Sigma-Aldrich Corporation) in phosphate buffered saline (PBS) and an aqueous solution of creatine (product of Sigma-Aldrich Corporation) in phosphate buffered saline (PBS) were provided as sample solutions. Their concentrations were set at 1.5 mg/dL and 1.0 mg/dL, respectively. These concentrations are values exceeding their normal levels a little. If measurement is feasible at these concentrations, the above-produced probes can be used for the measurement of creatinine and creatine. After the tip of the detection probe having the creatininase-containing sensitive film was immersed for five seconds in an aliquot (5 μL) of the creatinine-containing sample solution kept warm at 37° C. in a weighing dish, and the tip was pulled out of the sample solution, and fluorometric measurement was performed. PBS was provided as a control, fluorometric measurement was performed likewise. By the detection probe having the creatininase-free sensitive film, fluorometric measurement was also performed likewise.

Figure 32A:
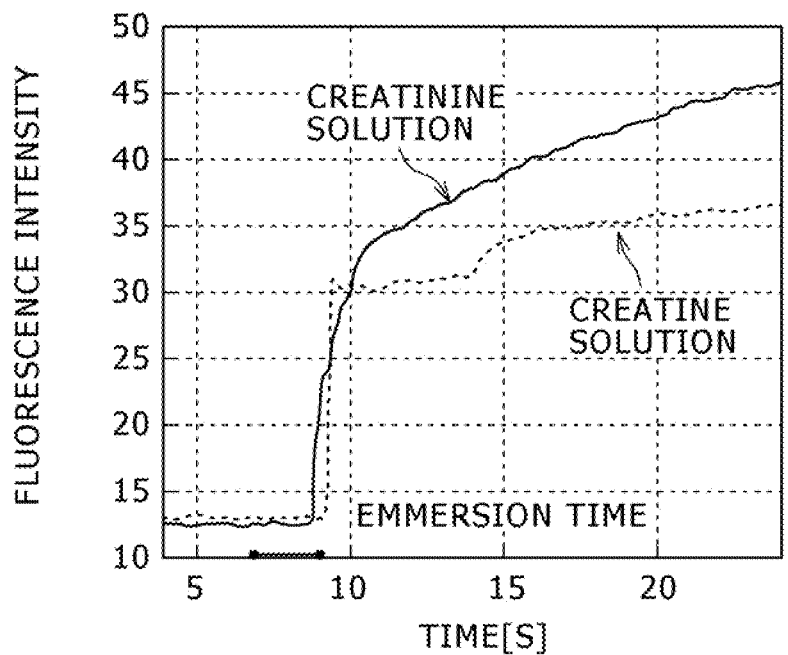
FIGS. 32A and 32B are graphs showing the results of fluorescence measurement in Example 18. Specifically.
Figure 32B:
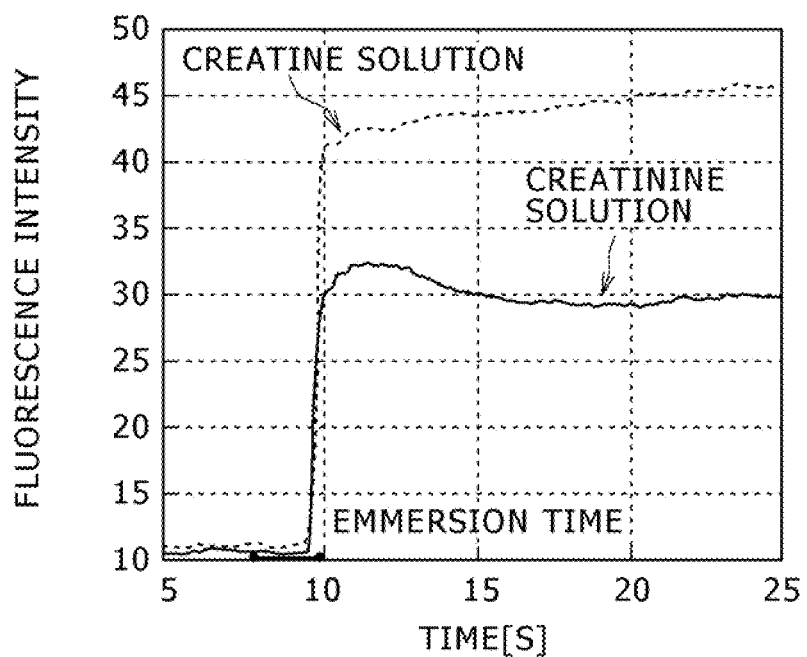

The results obtained by using the detection probe having the creatininase-containing sensitive film are shown in FIG. 32A, while the results obtained by using the detection probe having the creatininase-free sensitive film are shown in FIG. 32B.

When creatininase is not contained in a sensitive film, the intensity of fluorescence from a creatine solution is expected to become stronger compared with that available from a creatinine solution. From the results of FIG. 32B, it has been confirmed that the intensity of fluorescence from a creatine solution is strong.

When creatininase is contained in a sensitive film, this creatininase acts on creatine so that the intensity of fluorescence is expected to increase. From the results of FIG. 32A, it has been confirmed that the use of a creatininase-containing sensitive film leads to an increase in the intensity of fluorescence from a creatinine solution and can detect creatinine.

As appreciated from the foregoing, the enzyme reaction accelerates with an increase in the concentration of creatinine or creatine as a substrate, and therefore, the concentration of the substrate can be estimated from the concentration of a final product. Measurement was feasible at a concentration exceeding the normal value a little, so that at an abnormal value of a concentration higher than the above-mentioned concentration, measurement is feasible. It is possible to find the concentration of creatinine or creatine based on the intensity of fluorescence. Further, gingival crevicular fluid is known to be similar to the plasma component of blood. By measuring gingival crevicular fluid, the concentration of creatinine or creatine in blood can be quantified accordingly. It has, therefore, been confirmed that the probes each for detecting a substance in the body of this example can provide a technology that can measure the concentrations of creatinine and creatine in blood noninvasively rather than invasively.

Example 19

In this example, an experiment was conducted on a cholesterol detection system and a cholesterol ester detection system.

Firstly, sensitive parts were formed for the detection of cholesterol and a cholesterol ester, respectively. It is to be noted that three quarters of cholesterol in blood exist in the form of esters. Cholesterol esterase (product of Sigma-Aldrich Corporation), cholesterol oxidase (product of Sigma-Aldrich Corporation), peroxidase (POD, product of Sigma-Aldrich Corporation) and 10-acetyl-3,7-dihydroxyphenoxazine (ADHP, product of AnaSpec Inc.) were provided. A 1 U/μL aqueous solution of cholesterol esterase, a 0.5 U/μL aqueous solution of cholesterol oxidase, a 1.5 U/mL aqueous solution of peroxidase and a 50 μg/mL solution of ADHP in dimethyl sulfoxide (DMSO) were prepared.

Based on the above-prepared solutions, a cholesterol-esterase-containing aqueous solution was prepared by mixing an aliquot (10 μL) of the aqueous cholesterol-esterase solution, an aliquot (10 μL) of the aqueous cholesterol oxidase solution, an aliquot (15 μL) of the aqueous peroxidase solution and an aliquot (9 μL) of the ADHP solution and then adding purified water (270 μL) to the resulting mixture to dilute the same. On the other hand, a cholesterol-esterase-free aqueous solution was prepared by adding purified water (10 μL) in place of the aqueous cholesterol-esterase solution.

The photoimmobilizing solution (product of Girasol Bio Inc.) was added and mixed with each of the aqueous solutions such that the diazide compound amounted to 0.0625 wt %. As a result, a cholesterol-esterase-containing, "aqueous photo-immobilizing solution G" and a cholesterol-esterase-free, "aqueous photoimmobilizing solution GN" were prepared for the formation of sensitive parts.

Subsequently, two capillary portions of 0.4 mm in outer diameter and 3 cm in length were provided. Aliquots (0.2 μL) of the individual immobilizing solutions, that is, the aqueous photoimmobilizing solution G and aqueous photoimmobilizing solution GN were drawn up into the respective capillary portions. After being dried, the capillary portions were exposed to ultraviolet ray. As a result, a sensitive film of all the enzymes and the substrate and another sensitive film of the enzymes other than cholesterol esterase and the substrate were immobilized on the inner walls of the capillary portions, respectively, whereby sensitive parts were formed. In this manner, a detection probe having a cholesterol-esterase-containing sensitive film and a detection probe having a cholesterol-esterase-free sensitive film were produced.

Two probes each for detecting a substance in the body of this example were next produced in a similar manner as the production manner of the above-described probe for detecting a substance in the body of Example 15 except that the above-described sensitive parts for the detection of cholesterol and the cholesterol ester were employed. The probes were each optically connected an optical fiber fitted to a fluorophotometer with a built-in excitation light source and photodetector ("FLE-1000," trade name, manufactured by Nippon Sheet Glass Co., Ltd.). It is, therefore, possible to irradiate excitation light from the side wall of each capillary portion and to measure fluorescence produced from resorufin formed through the enzyme reactions in the capillary portion.

Cholesteryl stearate (product of Sigma-Aldrich Corporation) and cholesterol (product of Sigma-Aldrich Corporation) were suspended in ethanol, respectively. Those suspensions were combined together such that the content ratio of cholesteryl stearate to cholesterol became 4:1 as in blood. The resulting mixture was diluted with phosphate buffered saline (PBS) to prepare a mixed sample solution the concentration of which was 220 mg/dL in terms of cholesterol. In addition, a cholesterol sample solution was also provided, which contained only cholesterol at 220 mg/dL. 220 mg/dL or lower is the normal value. If measurement is feasible at this concentration, the above-produced probes can be used for the measurement of total cholesterol. After the tip of the detection probe having the cholesterol-esterase-containing sensitive film was immersed for 10 seconds in an aliquot (5 μL) of the mixed sample solution kept warm at 37° C. in a weighing dish, and the tip was pulled out of the sample solution, and fluorometric measurement was performed. The cholesterol sample solution was also measured likewise. PBS was provided as a control, measurement was also performed likewise. Further, the mixed sample solution, cholesterol sample solution and PBS were individually measured in a similar manner as mentioned above except that the detection probe was replaced by the detection probe having the cholesterol-esterase-free sensitive film.

Figure 33A:
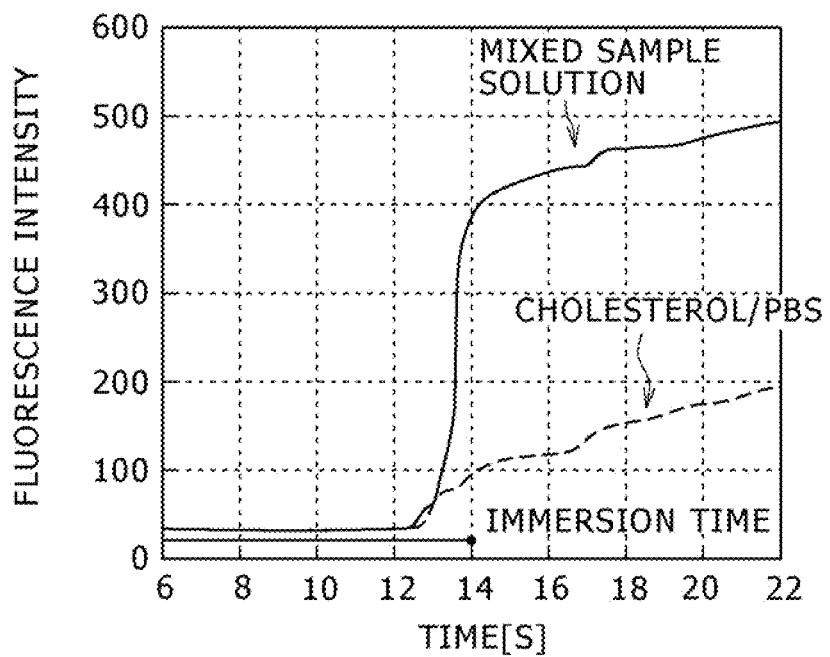
FIGS. 33A and 33B are graphs showing the results of fluorescence measurement in Example 19. Specifically.
Figure 33B:
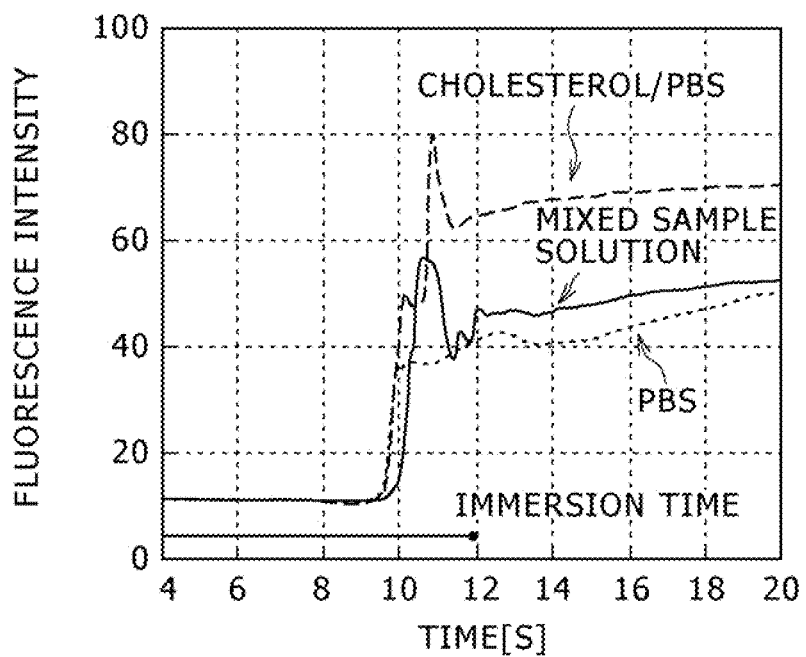

The results obtained by using the detection probe having the cholesterol-esterase-containing sensitive film are shown in FIG. 33A, while the results obtained by using the detection probe having the cholesterol-esterase-free sensitive film are shown in FIG. 33B.

When the detection probe having the cholesterol-esterase-containing sensitive film was used, the fluorescence intensity was high in the case of the mixed sample solution of the cholesteryl stearate and cholesterol. It was, therefore, confirmed that the reactions were more accelerated in the mixed sample solution than in the sample solution of cholesterol (see FIG. 33A). This can presumably be attributed to an increase in cholesterol produced as a result of the degradation of cholesteryl stearate by cholesterol esterase.

As cholesterol oxidase is incorporated in the sensitive film, the response to cholesterol is lower in the sample solution of cholesterol than in the mixed sample solution. It can be gathered that by cholesterol esterase, cholesterol was produced at a high concentration in the neighborhood of cholesterol oxidase in the sensitive film.

When the detection probe having the cholesterol-esterase-free sensitive film was used, on the other hand, the fluorescence intensity was lower in the case of the mixed sample solution than in the case of the sample solution containing only cholesterol. This is considered to be attributable to the lower concentration of cholesterol in the mixed sample solution. The results shown in FIG. 33B were as expected. Compared with the sample solution of cholesterol alone, the response to the mixed sample solution was low. The response to the mixed sample solution was, however, higher than that of PBS, so that the reactions are believed to have occurred.

As the enzyme reaction accelerates with an increase in the concentration of cholesterol as a substrate, the concentration of the substrate can be estimated from the concentration of a final product. Measurement was feasible at the normal value of 220 mg/dL, so that at an abnormal value of a concentration higher than the above-mentioned concentration, measurement is feasible. As it is possible to find the total concentration of cholesterol esters and cholesterol based on the intensity of fluorescence, the total amount of cholesterol can be determined. Further, gingival crevicular fluid is known to be similar to the plasma component of blood. By measuring gingival crevicular fluid, the total concentration of cholesterol in blood can be quantified accordingly. It has, therefore, been confirmed that the probes each for detecting a substance in the body can provide a technology that can measure the total concentration of cholesterol in blood noninvasively rather than invasively.

Example 20

Employed in this example were two probes each for detecting a substance in the body similar to that shown in FIG. 13, specifically a probe for detecting a substance in the body with an optical waveguide connected to a side cylindrical section of a capillary portion and another probe for detecting a substance in the body which was similar to the above-mentioned probe for detecting a substance in the body and was provided with a bore formed through the wall of the capillary portion.

1. Provision of Capillary Portions

Three capillary portions of 0.4 mm in outer diameter and 20 mm in length were provided. At a middle of one of the capillary portions (at a position spaced 10 mm from a tip), a bore of 0.05 mm in diameter and 0.2 mm in depth was formed. At a middle of another one of the capillary portions, a bore of 0.1 mm in diameter and 0.2 mm in depth was formed. As a result, vents were formed communicating the internal channels of the capillary portions and the outside with each other.

2. Preparation of Enzyme-Immobilizing Solution

Glucose oxidase (GOD, product of Sigma-Aldrich Corporation), peroxidase (POD, product of Sigma-Aldrich Corporation), ADHP (product of AnaSpec Inc.) and the photoimmobilizing solution (Hirasol Bio Inc.) were provided, and an enzyme-immobilizing solution was prepared.

3. Formation of Sensitive Film

The capillary portions provided with the vents were each sealed at the tips thereof with a sealant. Aliquots (5 μL) of the above-prepared, enzyme-immobilizing solution were provided in weighing dishes. An opposite tip of each of the capillary portions, which was on the unsealed side, was immersed in the enzyme-immobilizing solution, and the enzyme-immobilizing solution was drawn up into the capillary portion. After being dried, the capillary portion was exposed to ultraviolet ray. As a result, the enzymes were immobilized on the inner wall of the capillary portion to form a sensitive film.

The capillary portion provided with no vent was prepared, and the tip of the capillary portion was immersed in enzyme-immobilizing solution to form a sensitive film on the inner wall of the capillary portion.

4. Preparation of Sample Solution

A 1 g/dL solution of D-glucose in PBS was provided.

5. Observation of Response of Sensitive Film

An aliquot (5 μL) of the above-prepared sample solution (D-glucose solution) was provided in a weighing dish. One side of the capillary tube with the sensitive film arranged thereon, said one side being not the side through which the enzyme-immobilizing solution was drawn up, was immersed for five seconds in the enzyme-immobilizing solution, and fluorescence observation was conducted. A fluorescent stereomicroscope was provided for fluorescence observation. If the formed sensitive film responds to the D-glucose solution, ADHP changes to resorufin, and upon excitation by green light, orange fluorescence is produced. The excitation light and receiving fluorescence of the fluorescent stereomicroscope were set to green color and orange color, respectively.

Figure 34A:
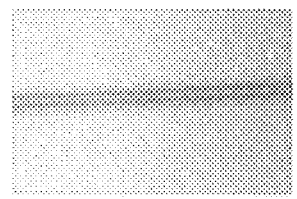
FIG. 34A shows a bright-field image and fluorescent image when a capillary portion making up a probe for detecting a substance in the body according to the present application was not provided with a vent.
Figure 34A:
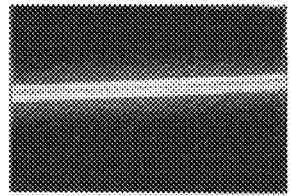
Figure 34B:
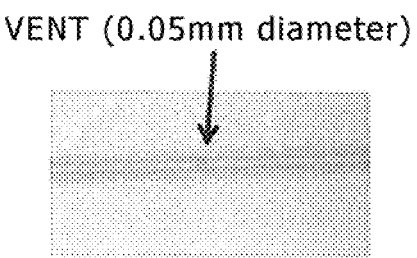
FIG. 34B shows a bright-field image and fluorescent image when a capillary portion making up a probe for detecting a substance in the body according to the present application was provided with a vent.
Figure 34B:
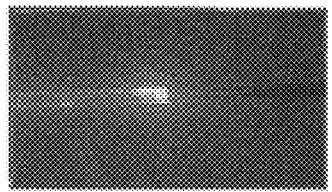

As a result, with the capillary portion provided with no vent, fluorescence was observed from the entire area of the inner wall of the capillary portion (see FIG. 34A). With each of the capillary portions provided with the vents (diameter: 0.05 mm and 0.1 mm), on the other hand, florescence was observed from the end, through which the enzyme-immobilizing solution was drawn up, to around the vent. The results obtained from the capillary portion provided with the 0.05 mm vent are shown in FIG. 34B. On each inner wall where fluorescence was observed, the corresponding sensitive film is believed to exist. It has been confirmed that, when a vent is provided, a sensitive film extends from a tip, through which an immobilizing solution is drawn up, to the vent. When no vent was provided, on the other hand, the sensitive film extended over the entire area of the capillary portion. It has, therefore, been confirmed that by providing a capillary portion, which is sealed at one thereof, with a vent, an enzyme-immobilizing solution is drawn up to around the vent through which air inside the internal channel can be released, but is hardly drawn up any further.

With the foregoing in view, the position of immobilization of a sensitive film on the inner wall of a capillary portion can be selectively determined by providing the capillary portion with plural vents. It is evident that the use of such vents upon attraction of an enzyme-immobilizing solution makes it possible to immobilize a sensitive film at a desired position such as between the tip and the proximal vent or between the vent and another one of the vents.

According to the present embodiments, a substance in the body in gingival crevicular fluid can be measured in the gingival sulcus. The substance in the body in the gingival crevicular fluid can, therefore, be measured in real time, with high accuracy, and noninvasively. The use of this technology makes it possible to contribute to improvements in analysis and/or diagnosis technologies in a wide variety of fields such as medical fields (pathology, tumor immunology, transplantation science, genetics, regenerative medicine, chemotherapy, and the like), drug development field, clinical test field, food field, agricultural field, engineering field, forensic medicine field, and crime lab field.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A probe for detecting a substance in the body in gingival crevicular fluid, comprising:
    a gingival sulcus insert section that can be inserted into a gingival sulcus; and
    a sensitive part arranged on the gingival sulcus insert section and containing a detection substance for permitting optical detection of the substance in the body,
    wherein the gingival sulcus insert section is provided with a capillary portion through which the gingival crevicular fluid can be collected under capillary action, and the gingival crevicular fluid is introduced to the sensitive part via the capillary portion, and
    wherein the sensitive part is arranged on an inner wall of the capillary portion, and the detection substance is immobilized in the sensitive part.

2. The probe according to claim 1, further comprising an optical waveguide for performing at least one of irradiation of light onto the sensitive part and detection of light from the sensitive part.

3. The probe according to claim 2, wherein the optical waveguide is formed from an optical fiber.

4. The probe according to claim 2, wherein the optical waveguide is connected to a cylindrical side wall of the capillary portion.

5. The probe according to claim 1, wherein the gingival sulcus insert section has a short side or short axis of not greater than 0.2 mm.

6. The probe according to claim 1, wherein the immobilization has been achieved through a photoreaction.

7. The probe according to claim 1, wherein the detection substance causes a change in fluorescence intensity when the detection substance specifically binds to the substance in the body.

8. The probe according to claim 7, wherein the detection substance is a boronic acid compound.

9. The probe according to claim 1, wherein the detection substance comprises:
    (1) at least one enzyme; and
    (2) a substance that can become a target of optical measurement.

10. The probe according to claim 9, wherein the substance that can become the target of the optical measurement is a substance that is converted to a fluorescence source through a reaction with hydrogen peroxide as a product of an enzyme reaction.

11. The probe according to claim 10, wherein the fluorescence source is resorufin.

12. The probe according to claim 9, wherein the substance that is capable of becoming the target of the optical measurement is a substance whose absorbance changes through a reaction with hydrogen peroxide as a product of an enzyme reaction.

13. The probe according to claim 12, wherein the substance whose absorbance changes is o-dianisidine.

14. The probe according to claim 11, wherein the enzymes comprise:
(1) a first enzyme for catalyzing a first reaction in which the substance in the body in the gingival crevicular fluid takes part, and a second enzyme for catalyzing a second reaction in which a product formed by the first reaction takes part; and
(2) a substance that can become a target of optical measurement.

15. The probe according to claim 14, wherein the first enzyme is selected from the group including glucose oxidase, alcohol oxidase, uricase (urate oxidase), lactate oxidase, fructosyl-amino acid oxidase, sarcosine oxidase, and cholesterol oxidase.

16. The probe according to claim 14, wherein the second enzyme is peroxidase.

17. A system for detecting a substance in the body for detecting a substance in the body in gingival crevicular fluid, comprising:
a probe for detecting a substance in the body provided with a gingival sulcus insert section that can be inserted into a gingival sulcus, and
a sensitive part arranged on the gingival sulcus insert section and containing a detection substance for permitting optical detection of the substance in the body, wherein the gingival sulcus insert section is provided with a capillary portion through which the gingival crevicular fluid can be collected under capillary action, and the gingival crevicular fluid is introduced to the sensitive part via the capillary portion, and wherein the sensitive part is arranged on an inner wall of the capillary portion, and the detection substance is immobilized in the sensitive part;
a light irradiator for irradiating light onto the sensitive part in the probe for detecting a substance in the body; and
a photodetector for detecting optical information from an inside of the sensitive part upon irradiation of light by the light irradiator.

18. The system according to claim 17, further comprising a dichroic element for extracting optical information from the inside of the sensitive part upon irradiation of light by the light irradiator.

* * * * *